United States Patent

Tanabe et al.

Patent Number: 5,965,611
Date of Patent: *Oct. 12, 1999

[54] PHARMACEUTICAL COMPOSITION FOR TREATING PERIPHERAL CIRCULATION DISORDERS

[75] Inventors: Hirofumi Tanabe; Toshinobu Murakami; Takashi Matsunaga; Shigeru Nakayama, all of Tokyo, Japan

[73] Assignees: Teigin Limited, Osaka; Taisho Pharmaceutical; Yutaka Mitzushima, both of Tokyo, all of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,174
[22] PCT Filed: Jun. 1, 1995
[86] PCT No.: PCT/JP95/01077
 § 371 Date: Dec. 2, 1996
 § 102(e) Date: Dec. 2, 1996
[87] PCT Pub. No.: WO95/33465
 PCT Pub. Date: Dec. 14, 1995

[30] Foreign Application Priority Data

Jun. 2, 1994 [JP] Japan .................................. 6-121260

[51] Int. Cl.⁶ .................................................. A61K 31/21
[52] U.S. Cl. ............................................................ 514/510
[58] Field of Search ............................................. 514/510

[56] References Cited

U.S. PATENT DOCUMENTS 5,124,352   6/1992   Mizushima et al. ..................... 514/510

FOREIGN PATENT DOCUMENTS

WO 86/07538   12/1986   WIPO .......................... A61K 31/557

OTHER PUBLICATIONS

International Search Report of PCT/JP95/01077 (Jun. 1995).

*Primary Examiner*—Raymond Henley, III
*Attorney, Agent, or Firm*—Sughrue, Mion, Zinn, Macpeak & Seas, PLLC

[57] ABSTRACT

A pharmaceutical composition for treating peripheral circulation disorders, which is an emulsion containing an isocarbacyclin having the following formula (1):

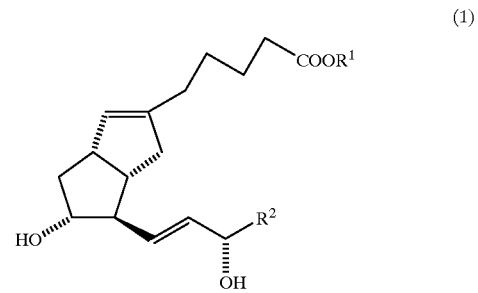

wherein $R^1$ is a hydrogen atom or alkyl group and $R^2$ is a alkyl group which may be substituted with, a alkenyl group or alkynyl group which may be substituted with, or a cycloalkyl group which may be substituted with, in an amount of 0.2 to 1,000 μg per ml of the composition, a vegetable oil in an amount of 0.05 to 0.5 g per ml of the composition, a phospholipid in an amount of 0.01 to 0.5 g per g of the vegetable oil, and water is provided.

7 Claims, 6 Drawing Sheets

PHARMACEUTICAL COMPOSITION FOR TREATING PERIPHERAL CIRCULATION DISORDERS

This application is a 371 of PCT/JP95/01077 filed Jun. 1, 1995.

TECHNICAL FIELD

The present invention relates to a pharmaceutical composition for treating chronic arterial occlusion. More specifically, it relates to a pharmaceutical composition for treating chronic arterial occlusion containing an isocarbacyclin as an effective ingredient.

BACKGROUND ART

Prostacyclin in the body is a local hormone mainly produced in the inside walls of the arteries and is an important factor in adjusting the functions of the body due to its powerful bioactivities, for example, activity in suppressing platelet aggregation and activity of vasodilation. It has been tried to use as a pharmaceutical. (P. J. Lewis & J. O. Grady, "Clinical Pharmacology of Prostacyclin", Raven Press, N.Y., 1981).

However, natural prostacyclin has an extremely easily hydrolyzed enol-ether bond in the molecule, so easily is inactivated in neutral or acid conditions and therefore cannot be said to be a preferable compound for a pharmaceutical due to its chemical instability. Therefore, chemically stable synthetic prostacyclin derivatives having bioactivity similar to natural prostacyclin have been studied at home and abroad (see R. C. Nickolson et al., Medicinal Research Reviews, vol. 5, p. 1, 1985). Among these, an isocarbacyclin, which is obtained by replacing the 6,9-position oxygen atom of prostacyclin with a methine group (—CH=group) and converting the 5,6-position double bond to a single bond, is a derivative which is chemically extremely stable and has a bioactivity comparable to natural prostacyclin. Application for pharmaceuticals is now being studied.

However, due to its powerful action in suppressing platelet aggregation and its peripheral vasodilation action, experiments as a clinical application of prostacyclin, are being tried to use for chronic arterial occlusion and other thrombotic disorders. Beraprost (tradename) ("The Japanese Journal of Clinical and Experimental Medicine", vol. 67, p. 574, 1990), Iloprost (tradename) ("The Japanese Journal of Clinical and Experimental Medicine", vol. 68, p. 1836, 1991), and other examples have been reported. The active ingredient of these, prostacyclin derivatives, however, is different in structure from the active ingredient of the present invention, that is, isocarbacyclin. The form of the preparation is also very different.

On the other hand, as a stabilized lipid preparation of prostaglandin derivatives, in recent years a lipid emulsion containing $PGE_1$ or $PGA_1$ has been proposed for the purpose of its vasodilation action, suppressing action of platelet aggregation and blood pressure reducing action etc. (see Japanese Unexamined Patent Publication (Kokai) No. 58-222014, Japanese Unexamined Patent Publication (Kokai) No. 59-141518, and Ann. Rheum. Diseases, 41 263 (1982); J. Pharm. Pharmacol., 35, 398 (1983)). This technique of making lipid preparations has been applied also to anticancer agents and proposals have been made to raise the selective transfer of the anticancer agent to the target organ (see Japanese Unexamined Patent Publication (Kokai) No. 59-122423). However, since prostacyclin is chemically unstable, it has been difficult to make a lipid emulsion. Therefore, attempts have been made to make isocarbacyclin a lipid emulsion and a more effective, stable preparation having a sustained action and having a targeting effect has been developed (Japanese Unexamined Patent Publication (Kokai) No. 61-289034).

Also known are examples of use of $LipoPGE_1$ using the form of a lipid emulsion for chronic arterial occlusion ("The Japanese Journal of Clinical and Experimental Medicine", vol. 63, p. 2423, 1986, "Cardioangiology", vol. 20, p. 331, 1986).

DISCLOSURE OF INVENTION

An object of the present invention is to provide a pharmaceutical composition for treating chronic arterial occlusion.

A still further object of the present invention is to provide a pharmaceutical composition for treating chronic arterial occlusion containing isocarbacyclin derivatives which consist of a specific structure, superior in safety, and in the form of a lipid emulsion.

Other objects and advantages of the present invention will become clear from the following explanation.

In accordance with the present invention, the above objects and advantages of the present invention are, first, achieved by a pharmaceutical composition for treating chronic arterial occlusion comprising an emulsion containing an isocarbacyclin, having the following formula (1):

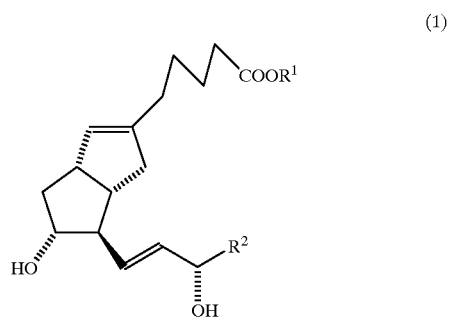

(1)

wherein $R^1$ is a hydrogen atom or a $C_1$ to $C_{10}$ alkyl group and $R^2$ is a $C_1$ to $C_{13}$ alkyl group which may be substituted, a $C_2$ to $C_{13}$ alkenyl group or alkynyl group which may be substituted or a $C_3$ to $C_{10}$ cycloalkyl group which may be substituted, in an amount of 0.2 to 1,000 μg per ml of the composition, a vegetable oil in an amount of 0.05 to 0.5 g per ml of the composition, a phospholipid in an amount of 0.01 to 0.5 g per g of the vegetable oil, and water.

BEST MODE FOR CARRYING OUT THE INVENTION

Figure 1:
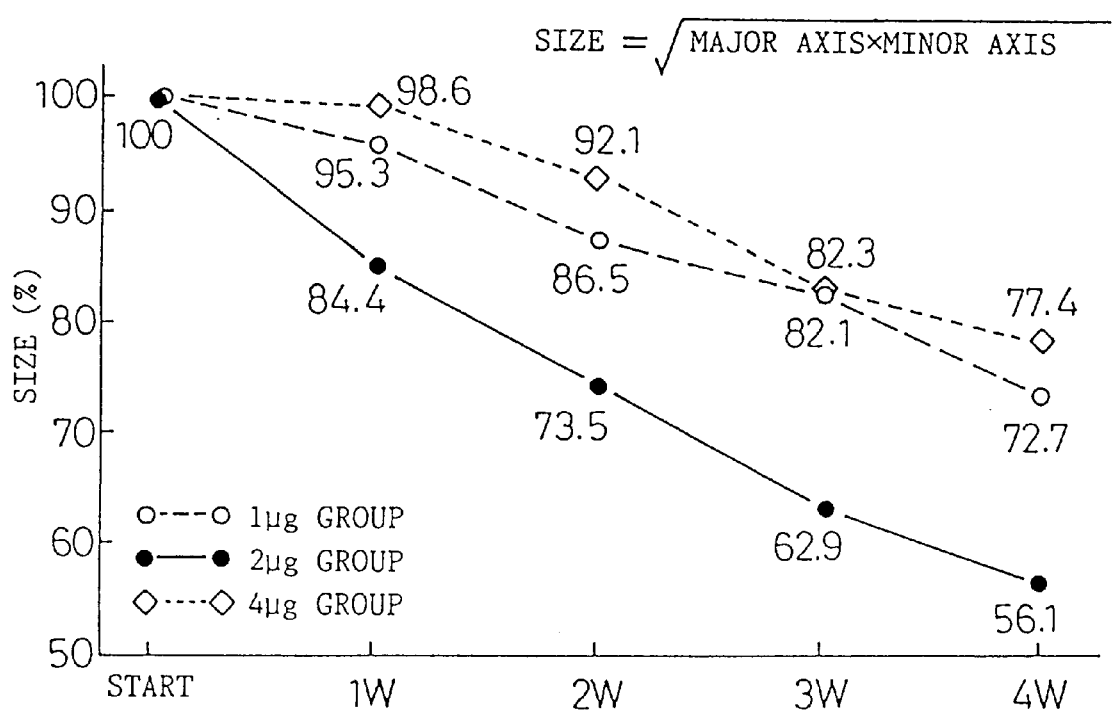
FIG. 1 is a view illustrating the trends in the size of ulcers in the case of using the lipid emulsion of the present invention for patients suffering from chronic arterial occlusion.

The isocarbacyclin used in the present invention is expressed by the above formula (1).

In the above formula (1), $R^1$ is a hydrogen atom or a $C_1$ to $C_{10}$ alkyl group. The $C_1$ to $C_{10}$ alkyl group may be either straight chained or branched. As the alkyl group, for example, methyl, ethyl, n-propyl, iso-propyl, n-butyl, sec-butyl, tert-butyl, n-pentyl, n-heptyl, n-octyl, and n-decyl may be mentioned. Among these, a $C_1$ to $C_6$ alkyl group, particularly a $C_1$ to $C_4$ alkyl group, is preferred. Among these as well, as $R^1$, a hydrogen atom or methyl group is preferred and a methyl group is particularly preferred.

In formula (1), $R^2$ is a $C_1$ to $C_{13}$ alkyl group which may be substituted, a $C_2$ to $C_{13}$ alkenyl group or alkynyl group which may be substituted, or a $C_3$ to $C_{10}$ cycloalkyl group which may be substituted.

Any group of the $C_1$ to $C_{13}$ alkyl group, $C_2$ to $C_{13}$ alkenyl group and alkynyl group is possible to be substituted for $R^2$, but preferably —$R^2$ is —$CH_2CH_2R^{21}$ or —$CH_2CH(CH_3)R^{22}$. Here, $R^{21}$ and $R^{22}$ is a $C_1$ to $C_{10}$ alkyl group which may be substituted or a $C_2$ to $C_{10}$ alkenyl group or an alkynyl group which may be substituted.

As the $C_1$ to $C_{10}$ alkyl group not substituted for $R^{21}$ and $R^{22}$, for example, a methyl group, ethyl group, n-propyl group, iso-propyl group, n-butyl group, sec-butyl group, tert-butyl group, n-pentyl group, 2-methylbutyr-4-yl group, 3-methylbutyr-4-yl group, 4-methylbutyr-4-yl group, n-hexyl group, 2-methylpentyr-5-yl group, 3-methylpentyr-5-yl group, 4-methylpentyr-5-yl group, 5-methylpentyr-5-yl group, n-heptyl group, 2-methylhexyr-6-yl group, 3-methylhexyr-6-yl group, 4-methylhexyr-6-yl group, 5-methylhexyr-6-yl group, 6-methylhexyr-6-yl group, etc. may be mentioned.

Further, as the $C_2$ to $C_{10}$ alkenyl group not substituted for $R^{21}$ and $R^{22}$, for example, a 1-methylvinyl group, vinyl group, 1-propenyl group, 1-butenyl group, 1-pentenyl group, 1-hexenyl group, 1-heptenyl group, allyl group, methallyl group, 2-butenyl group, 2-pentenyl group, 2-hexenyl group, 2-heptenyl group, 1-penten-2-yl group, 3-methyl-1-buten-1-yl group, 3-methyl-1-penten-1-yl group, 4-methyl-1-penten-1-yl group, 3-methyl-1-hexen-1-yl group, 4-methyl-1-hexen-1-yl group, 3-methyl-1-yl group, 5-methyl-1-hepten-1-yl group, 3,3-dimethyl-1-hepten-1-yl group, 2-penten-3-yl group, 3-methyl-2-butenyl group, 4-methyl-2-pentenyl group, 4-methyl-2-hexenyl group, 5-methyl-2-heptenyl group, 4,4-dimethyl-2-hexenyl group, 1-buten-4-yl group, 2-methyl-1-buten-4-yl group, 3-methyl-1-buten-4-yl group, 2-penten-4-yl group, 3-hexenyl group, 3-heptenyl group, 3,3-dimethyl-1-buten-4-yl group, 1-penten-5-yl group, 4-methyl-penten-5-yl group, 4,4-dimethyl-penten-5-yl group, 3-methyl-penten-5-yl group, 2-methyl-penten-5-yl group, 2-hexen-6-yl group, 2-methyl-2-hexen-6-yl group, 5-methyl-2-hexen-6-yl group, 5,5-dimethyl-2-hexen-6-yl group, 4-ethyl-3-hexenyl group, 4-methyl-3-hexenyl group, 2-methyl-2-pentene group, 2-methyl-3-hexenyl group, 5-methyl-3-hexenyl group, 2-methyl-3-heptenyl group, 6-methyl-3-heptenyl group, 2,5-dimethyl-2-hexen-6-yl group, 2-methyl-2-hepten-6-yl group, 2,6-dimethyl-2-hepten-6-yl group, 3-hepten-7-yl group, 3-methyl-hepten-7-yl group, 3-ethyl-hepten-7-yl group, 5-methyl-hepten-7-yl group, 6-methyl-hepten-7-yl group, 6,6-dimethyl-hepten-7-yl group etc. may be mentioned.

Further, as the $C_2$ to $C_{10}$ alkynyl group not substituted for $R^{21}$ and $R^{22}$, for example, an ethynyl group, 1-propyn-3-yl group, butynyl group, pentynyl group, hexynyl group, heptynyl group, 3-methyl-butynyl group, 3,3-dimethyl-butynyl group, 3-methyl-pentynyl group, 3,3-dimethyl-pentynyl group, 3-ethyl-pentynyl group, 4-methyl-pentynyl group, 4,4-dimethyl-pentynyl group, 3-methyl-hexynyl group, 3,3-dimethyl-hexynyl group, 5-methyl-hexynyl group, 5,5-dimethyl-hexynyl group, 3-methyl-heptynyl group, 3,3-dimethyl-heptynyl group, 5-methyl-heptynyl group, 5-ethyl-heptynyl group, 5,5-dimethyl-heptynyl group, 1-propyn-3-yl group, 1-butyn-3-yl group, 2-pentyn-3-yl group, 2-butyn-1-yl group, 2-pentyn-1-yl group, 4-methyl-2-pentyn-1-yl group, 4,4-dimethyl-2-pentyn-1-yl group, 2-hexyn-1-yl group, 4-methyl-2-hexyn-1-yl group, 4-ethyl-2-hexyn-1-yl group, 4,4-dimethyl-2-hexyn-1-yl group, 2-heptyn-1-yl group, 3-octyn-2-yl group, 4-methyl-2-heptyn-1-yl group, 4,4-dimethyl-2-heptyn-1-yl group, 5,5-dimethyl-2-heptyn-1-yl group, 5-ethyl-2-heptyn-1-yl group, 3-heptyn-2-yl group, 1-butyn-4-yl group, 1-pentyn-4-yl group, 3-methyl-1-butyn-4-yl group, 2-pentyn-5-yl group, 3-hexyn-1-yl group, 5-methyl-3-hexyn-1-yl group, 2-methyl-3-hexyn-1-yl group, 5,5-dimethyl-3-hexyn-1-yl group, 2,2-dimethyl-3-hexyn-1-yl group, 3-heptyn-1-yl group, 4-octyn-2-yl group, 2-methyl-4-octyn-2-yl group, 2,2-dimethyl-3-heptyn-1-yl group, 2-methyl-3-heptyn-1-yl group, 5-methyl-3-heptyn-1-yl group, 2-hexyn-5-yl group, 5-ethyl-3-heptyn-1-yl group, 6-methyl-3-heptyn-1-yl group, 6,6-dimethyl-3-heptyn-1-yl group, 1-pentyn-5-yl group, 1-hexyn-5-yl group, 4-methyl-1-pentyn-5-yl group, 4,4-dimethyl-1-pentyn-5-yl group, 3-methyl-1-pentyn-5-yl group, 3,3-dimethyl-1-pentyn-5-yl group, 2-hexyn-6-yl group, 2-heptyn-6-yl group, 5-methyl-2-hexyn-6-yl group, 5,5-dimethyl-2-hexyn-6-yl group, 4-methyl-2-hexyn-6-yl group, 4,4-dimethyl-2-hexyn-6-yl group, 3-heptyn-7-yl group, 3-octyn-7-yl group, 6-methyl-3-heptyn-7-yl group, 6,6-dimethyl-3-heptyn-7-yl group, 5-methyl-3-heptyn-7-yl group, 2-methyl-3-heptyn-7-yl group, 2,2-dimethyl-3-heptyn-7-yl group, 1-hexyn-6-yl group, 1-heptyn-6-yl group, 6-methyl-1-heptyn-6-yl group, 5-methyl-1-hexyn-6-yl group, 5,5-dimethyl-1-hexyn-6-yl group, 4-methyl-1-hexyn-6-yl group, 3-methyl-1-hexyn-6-yl group, 3,3-dimethyl-1-hexyn-6-yl group, 2-heptyn-7-yl group, 2-octyn-7-yl group, 7-methyl-2-octyn-7-yl group, 5,5-dimethyl-2-heptyn-7-yl group, 4-methyl-2-heptyn-7-yl group, 4,4-dimethyl-2-heptyn-7-yl group, 1-heptyn-7-yl group, 1-octyn-7-yl group, 7-methyl-1-octyn-7-yl group, 5-methyl-1-heptyn-7-yl group, 4-methyl-1-heptyn-7-yl group, 3-methyl-1-heptyn-7-yl group, 3,3-dimethyl-1-heptyn-7-yl group, 4,4-dimethyl-1-heptyn-7-yl group etc. may be mentioned.

Further, as the substituent for $R^{21}$ and $R^{22}$, a fluorine, chlorine, or other halogen atom; a methoxy, ethoxy, propoxy, butoxy group, or other lower alkoxy group, etc. may be mentioned. Concrete examples of substitution by a halogen atom are those introduced fluorine in the form of a trifluoromethyl group.

These $R^{21}$ and $R^{22}$ preferably represent a $C_1$ to $C_5$ straight chain or branched alkyl group. As the $C_1$ to $C_5$ alkyl group, for example, a methyl group, ethyl group, n-propyl group, iso-propyl group, n-butyl group, sec-butyl group, tert-butyl group, n-pentyl group, etc. may be mentioned. Among these, as $R^{21}$ or $R^{22}$, a $C_3$ to $C_5$ alkyl group is preferable, an n-propyl group or n-butyl group is more preferable, and an n-butyl group is particularly preferable. In particular, as the $R^{21}$, an n-propyl group is preferable, while as the $R^{22}$, an n-butyl group is preferable.

Further, as the $C_3$ to $C_{10}$ cycloalkyl group $R^2$ which may be substituted with, for example, a cyclopentyl, cyclohexyl group, etc. may be mentioned. Among these, a $C_3$ to $C_8$ cycloalkyl group, in particular a $C_4$ to $C_7$ cycloalkyl group, is preferable. As the substituent of the cycloalkyl groups, for example, a methyl, ethyl, propyl, hexyl group, or other $C_1$ to $C_6$ lower alkyl group; a fluorine, chlorine, or other halogen atom; a methoxy, ethoxy, propoxy, butoxy group, or other lower alkoxy group; a trifluoromethyl group and other halogenated lower alkyl groups etc. may be mentioned.

Among these, as $R^2$, an n-pentyl, 2-methylhexyl, or cyclopentyl group is particularly preferable. Further, a combination where $R^1$ is the methyl group and $R^2$ is an n-pentyl group is preferable.

Specific examples of the isocarbacyclin having the above formula (1) are as follows:

(1) 9(O)-methano-$\Delta^{6(9\alpha)}$-prostaglandin $I_1$ (2) 20-methyl-9(O)-methano-$\Delta^{6(9\alpha)}$-prostaglandin $I_1$ (3) 19,20-dinol-9(O)-methano-$\Delta^{6(9\alpha)}$-prostaglandin $I_1$ (4) 20-nol-9(O)-methano-$\Delta^{6(9\alpha)}$-prostaglandin $I_1$ (5) 19-methyl-9(O)-methano-$\Delta^{6(9\alpha)}$-prostaglandin $I_1$ (6) 18-methyl-9(O)-methano-$\Delta^{6(9\alpha)}$-prostaglandin $I_1$ (7) 20-ethyl-9(O)-methano-$\Delta^{6(9\alpha)}$-prostaglandin $I_1$ (8) 20-isopropyl-9(O)-methano-$\Delta^{6(9\alpha)}$-prostaglandin $I_1$ (9) 20-methyl-20-ethyl-9(O)-methano-$\Delta^{6(9\alpha)}$-prostaglandin $I_1$

(10) 19-methyl-20-ethyl-9(O)-methano-$\Delta^{6(9\alpha)}$-prostaglandin $I_1$

(11) 18-methyl-20-ethyl-9(O)-methano-$\Delta^{6(9\alpha)}$-prostaglandin $I_1$

(12) 20-propyl-9(O)-methano-$\Delta^{6(9\alpha)}$-prostaglandin $I_1$

(13) 22-methyl-20-propyl-9(O)-methano-$\Delta^{6(9\alpha)}$-prostaglandin $I_1$

(14) 21-methyl-20-propyl-9(O)-methano-$\Delta^{6(9\alpha)}$-prostaglandin $I_1$

(15) 20-methyl-20-propyl-9(O)-methano-$\Delta^{6(9\alpha)}$-prostaglandin $I_1$

(16) 19-methyl-20-propyl-9(O)-methano-$\Delta^{6(9\alpha)}$-prostaglandin $I_1$

(17) 18-methyl-20-propyl-9(O)-methano-$\Delta^{6(9\alpha)}$-prostaglandin $I_1$

(18) 20-nol-18-methylene-9(O)-methano-$\Delta^{6(9\alpha)}$-prostaglandin $I_1$

(19) $^{20}$-nol-18,19-dehydro-9(O)-methano-$\Delta^{6(9\alpha)}$-prostaglandin $I_1$

(20) 18,19-dehydro-9(O)-methano-$\Delta^{6(9\alpha)}$-prostaglandin $I_1$

(21) 18,19-dehydro-20-methyl-9(O)-methano-$\Delta^{6(9\alpha)}$-prostaglandin $I_1$

(22) 18,19-dehydro-20-ethyl-9(O)-methano-$\Delta^{6(9\alpha)}$-prostaglandin $I_1$

(23) 18,19-dehydro-20-propyl-9(O)-methano-$\Delta^{6(9\alpha)}$-prostaglandin $I_1$

(24) 18,19-dehydro-20-butyl-9(O)-methano-$\Delta^{6(9\alpha)}$-prostaglandin $I_1$

(25) 18-methylene-20-methyl-9(O)-methano-$\Delta^{6(9\alpha)}$-prostaglandin $I_1$

(26) 18,19-dehydro-20,20-dimethyl-9(O)-methano-$\Delta^{6(9\alpha)}$-prostaglandin $I_1$

(27) 18,19-dehydro-20-methyl-20-ethyl-9(O)-methano-$\Delta^{6(9\alpha)}$-prostaglandin $I_1$

(28) 18,19-dehydro-20-isopropyl-20-ethyl-9(O)-methano-$\Delta^{6(9\alpha)}$-prostaglandin $I_1$

(29) 18,19-dehydro-20-methyl-20-butyl-9(O)-methano-$\Delta^{6(9\alpha)}$-prostaglandin $I_1$

(30) 18,19-dehydro-20-(1-methylpropyl)-9(O)-methano-$\Delta^{6(9\alpha)}$-prostaglandin $I_1$

(31) 18,19-dehydro-20-methyl-20-propyl-9(O)-methano-$\Delta^{6(9\alpha)}$-prostaglandin $I_1$

(32) 18,19-dehydro-20,20-dimethyl-20-butyl-9(O)-methano-$\Delta^{6(9\alpha)}$-prostaglandin $I_1$

(33) 19,20-dehydro-9(O)-methano-$\Delta^{6(9\alpha)}$-prostaglandin $I_1$

(34) 19,20-dehydro-20-methyl-9(O)-methano-$\Delta^{6(9\alpha)}$-prostaglandin $I_1$

(35) 19,20-dehydro-19-methyl-9(O)-methano-$\Delta^{6(9\alpha)}$-prostaglandin $I_1$

(36) 19,20-dehydro-20-ethyl-9(O)-methano-$\Delta^{6(9\alpha)}$-prostaglandin $I_1$

(37) 19,20-dehydro-20-propyl-9(O)-methano-$\Delta^{6(9\alpha)}$-prostaglandin $I_1$

(38) 19,20-dehydro-20-butyl-9(O)-methano-$\Delta^{6(9\alpha)}$-prostaglandin $I_1$

(39) 19,20-dehydro-18,20-dimethyl-9(O)-methano-$\Delta^{6(9\alpha)}$-prostaglandin $I_1$

(40) 19,20-dehydro-20-(1-methylpropyl)-9(O)-methano-$\Delta^{6(9\alpha)}$-prostaglandin $I_1$

(41) 19,20-dehydro-20-isopropyl-9(O)-methano-$\Delta^{6(9\alpha)}$-prostaglandin $I_1$

(42) 19,20-dehydro-20-(2-methylbutyl)-9(O)-methano-$\Delta^{6(9\alpha)}$-prostaglandin $I_1$

(43) 19,20-dehydro-20-(1,1-dimethylpropyl)-9(O)-methano-$\Delta^{6(9\alpha)}$-prostaglandin $I_1$

(44) 20-methylene-9(O)-methano-$\Delta^{6(9\alpha)}$-prostaglandin $I_1$

(45) 20-methyl-20-methylene-9(O)-methano-$\Delta^{6(9\alpha)}$-prostaglandin $I_1$

(46) 19-methyl-20-methylene-9(O)-methano-$\Delta^{6(9\alpha)}$-prostaglandin $I_1$

(47) 20-ethylidene-9(O)-methano-$\Delta^{6(9\alpha)}$-prostaglandin $I_1$

(48) 20-propylidene-9(O)-methano-$\Delta^{6(9\alpha)}$-prostaglandin $I_1$

(49) 20-butylidene-9(O)-methano-$\Delta^{6(9\alpha)}$-prostaglandin $I_1$

(50) 20-(1-ethylbutylidene)-9(O)-methano-$\Delta^{6(9\alpha)}$-prostaglandin $I_1$

(51) 20-(1-methylbutylidene)-9(O)-methano-$\Delta^{6(9\alpha)}$-prostaglandin $I_1$

(52) 20-(1-methylethylidene)-9(O)-methano-$\Delta^{6(9\alpha)}$-protaglandin $I_1$

(53) 19-methyl-20-propylidene-9(O)-methano-$\Delta^{6(9\alpha)}$-prostaglandin $I_1$

(54) 20-(2-methylpropylidene)-9(O)-methano-$\Delta^{6(9\alpha)}$-prostaglandin $I_1$

(55) 19-methyl-20-butylidene-9(O)-methano-$\Delta^{6(9\alpha)}$-prostaglandin $I_1$

(56) 20-(3-methylbutylidene)-9(O)-methano-$\Delta^{6(9\alpha)}$-prostaglandin $I_1$

(57) 19,19-dimethyl-20-methylene-9(O)-methano-$\Delta^{6(9\alpha)}$-prostaglandin $I_1$

(58) 20-vinyl-9(O)-methano-$\Delta^{6(9)\alpha}$-prostaglandin $I_1$

(59) 19-methyl-20-vinyl-9(O)-methano-$\Delta^{6(9)\alpha}$-prostaglandin $I_1$

(60) 19,19-dimethyl-20-vinyl-9(O)-methano-$\Delta^{6(9)\alpha}$-prostaglandin $I_1$

(61) 20-methyl-20-vinyl-9(O)-methano-$\Delta^{6(9)\alpha}$-prostaglandin $I_1$

(62) 20-(1-methylvinyl)-9(O)-methano-$\Delta^{6(9)\alpha}$-prostaglandin $I_1$

(63) 20-(1-propenyl)-9(O)-methano-$\Delta^{6(9)\alpha}$-prostaglandin $I_1$

(64) 20-(2-methyl-1-propenyl)-9(O)-methano-$\Delta^{6(9)\alpha}$-prostaglandin $I_1$

(65) 19-methyl-20-(1-propenyl)-9(O)-methano-$\Delta^{6(9)\alpha}$-prostaglandin $I_1$

(66) 19,19-dimethyl-20-(1-propenyl)-9(O)-methano-$\Delta^{6(9\alpha)}$-prostaglandin $I_1$

(67) 19-methyl-20-(2-methyl-1-propenyl)-9(O)-methano-$\Delta^{6(9)\alpha}$-prostaglandin $I_1$

(68) 18-methyl-20-(2-methyl-1-propenyl)-9(O)-methano-$\Delta^{6(9)\alpha}$-prostaglandin $I_1$

(69) 18,18-dimethyl-20-(2-methyl-1-propenyl)-9(O)-methano-$\Delta^{6(9)\alpha}$-prostaglandin $I_1$

(70) 20-(1-butenyl)-9(O)-methano-$\Delta^{6(9)\alpha}$-prostaglandin $I_1$

(71) 20-(2-methyl-1-butenyl)-9(O)-methano-$\Delta^{6(9)\alpha}$-prostaglandin $I_1$

(72) 20-(2-ethyl-1-butenyl)-9(O)-methano-$\Delta^{6)9\alpha}$-prostaglandin $I_1$

(73) 20-methyl-20-butenyl-9(O)-methano-$\Delta^{6(9)\alpha}$-prostaglandin $I_1$

(74) 19-methyl-20-butenyl-9(O)-methano-$\Delta^{6(9)\alpha}$-prostaglandin $I_1$

(75) 19,19-dimethyl-20-butenyl-9(O)-methano-$\Delta^{6(9)\alpha}$-prostaglandin $I_1$

(76) 20-nol-18,19-tetradehydro-9(O)-methano-$\Delta^{6(9)\alpha}$-prostaglandin $I_1$

(77) 18,19-tetradehydro-9(O)-methano-$\Delta^{6(9)\alpha}$-prostaglandin $I_1$

(78) 18,19-tetradehydro-20-methyl-9(O)-methano-$\Delta^{6(9\alpha)}$-prostaglandin $I_1$

(79) 18,19-tetradehydro-20-ethyl-9(O)-methano-$\Delta^{6(9)\alpha}$-prostaglandin $I_1$

(80) 18,19-tetradehydro-20-butyl-9(O)-methano-$\Delta^{6(9)\alpha}$-prostaglandin $I_1$

(81) 18,19-tetradehydro-20-propyl-9(O)-methano-$\Delta^{6(9)\alpha}$-prostaglandin $I_1$

(82) 18,19-tetradehydro-20,20-dimethyl-9(O)-methano-$\Delta^{6(9)\alpha}$-prostaglandin $I_1$

(83) 18,19-tetradehydro-20,20,20-trimethyl-9(O)-methano-$\Delta^{6(9)\alpha}$-prostaglandin $I_1$

(84) 18,19-tetradehydro-20-methyl-20-ethyl-9(O)-methano-$\Delta^{6(9)\alpha}$-prostaglandin $I_1$

(85) 18,19-tetradehydro-20,20-dimethyl-20-ethyl-9(O)-methano-$\Delta^{6(9)\alpha}$-prostaglandin $I_1$

(86) 18,19-tetradehydro-20,20-diethyl-9(O)-methano-$\Delta^{6(9\alpha)}$-prostaglandin $I_1$

(87) 18,19-tetradehydro-20-isopropyl-9(O)-methano-$\Delta^{6(9\alpha)}$-prostaglandin $I_1$

(88) 18,19-tetradehydro-20-t-butyl-9(O)-methano-$\Delta^{6(9\alpha)}$-prostaglandin $I_1$

(89) 18,19-tetradehydro-20-methyl-20-propyl-9(O)-methano-$\Delta^{6(9)\alpha}$-prostaglandin $I_1$

(90) 18,19-tetradehydro-20,20-dimethyl-20-propyl-9(O)-methano-$\Delta^{6(9)\alpha}$-prostaglandin $I_1$

(91) 18,19-tetradehydro-20-(2-methylpropyl)-9(O)-methano-$\Delta^{6(9)\alpha}$-prostaglandin $I_1$

(92) 18,19-tetradehydro-20-(2,2-dimethylpropyl)-9(O)-methano-$\Delta^{6(9)\alpha}$-prostaglandin $I_1$

(93) 18,19-tetradehydro-20-methyl-20-butyl-9(O)-methano-$\Delta^{6(9)\alpha}$-prostaglandin $I_1$

(94) 18,19-tetradehydro-20,20-dimethyl-20-butyl-9(O)-methano-$\Delta^{6(9)\alpha}$-prostaglandin $I_1$

(95) 18,19-tetradehydro-20-(2-methylbutyl)-9(O)-methano-$\Delta^{6(9)\alpha}$-prostaglandin $I_1$

(96) 18,19-tetradehydro-20-(2-ethylbutyl)-9(O)-methano-$\Delta^{6(9)\alpha}$-prostaglandin $I_1$

(97) 18,19-tetradehydro-20-(2,2-dimethylbutyl)-9(O)-methano-$\Delta^{6(9)\alpha}$-prostaglandin $I_1$

(98) 19,20-tetradehydro-9(O)-methano-$\Delta^{6(9)\alpha}$-prostaglandin $I_1$

(99) 19,20-tetradehydro-18-methyl-9(O)-methano-$\Delta^{6(9\alpha)}$-prostaglandin $I_1$ (100) 19,20-tetradehydro-18,20-dimethyl-9(O)-methano-$\Delta^{6(9)\alpha}$-prostaglandin $I_1$ (101) 19,20-tetradehydro-20-methyl-9(O)-methano-$\Delta^{6(9\alpha)}$-prostaglandin $I_1$ (102) 19,20-tetradehydro-20-ethyl-9(O)-methano-$\Delta^{6(9)\alpha}$-prostaglandin $I_1$ (103) 19,20-tetradehydro-20-isopropyl-9(O)-methano-$\Delta^{6(9\alpha)}$-prostaglandin $I_1$ (104) 19,20-tetradehydro-20-t-butyl-9(O)-methano-$\Delta^{6(9\alpha)}$-prostaglandin $I_1$ (105) 19,20-tetradehydro-20-propyl-9(O)-methano-$\Delta^{6(9\alpha)}$-prostaglandin $I_1$ (106) 19,20-tetradehydro-20-(1-methylpropyl)-9(O)-methano-$\Delta^{6(9)\alpha}$-prostaglandin $I_1$ (107) 19,20-tetradehydro-20-(1-ethylpropyl)-9(O)-methano-$\Delta^{6(9)\alpha}$-prostaglandin $I_1$ (108) 19,20-tetradehydro-20-(1,1-dimethylpropyl)-9(O)-methano-$\Delta^{6(9)\alpha}$-prostaglandin $I_1$ (109) 19,20-tetradehydro-20-butyl-9(O)-methano-$\Delta^{6(9)\alpha}$-prostaglandin $I_1$ (110) 19,20-tetradehydro-18-dimethyl-20-butyl-9(O)-methano-$\Delta^{6(9)\alpha}$-prostaglandin $I_1$ (111) 19,20-tetradehydro-20-(1-methylbutyl)-9(O)-methano-$\Delta^{6(9)\alpha}$-prostaglandin $I_1$ (112) 19,20-tetradehydro-20-(1,1-dimethylbutyl)-9(O)-methano-$\Delta^{6(9)\alpha}$-prostaglandin $I_1$ (113) 19,20-tetradehydro-20-(2,2-dimethylbutyl)-9(O)-methano-$\Delta^{6(9)\alpha}$-prostaglandin $I_1$ (114) 19,20-tetradehydro-20-(2-ethylbutyl)-9(O)-methano-$\Delta^{6(9)\alpha}$-prostaglandin $I_1$ (115) 19,20-tetradehydro-18-methyl-20-propyl-9(O)-methano-$\Delta^{6(9)\alpha}$-prostaglandin $I_1$ (116) 20-methylidine-9(O)-methano-$\Delta^{6(9)\alpha}$-prostaglandin $I_1$ (117) 20-methylidine-18-methyl-9(O)-methano-$\Delta^{6(9)\alpha}$-prostaglandin $I_1$ (118) 20-methylidine-20-methyl-9(O)-methano-$\Delta^{6(9)\alpha}$-prostaglandin $I_1$ (119) 20-ethylidine-9(O)-methano-$\Delta^{6(9)\alpha}$-prostaglandin $I_1$ (120) 20-propylidine-9(O)-methano-$\Delta^{6(9\alpha)}$-prostaglandin I$_1$ (121) 20-(2-methylpropylidine)-9(O)-methano-$\Delta^{6(9\alpha)}$-protaglandin I$_1$ (122) 20-propylidine-19-methyl-9(O)-methano-$\Delta^{6(9\alpha)}$-prostaglandin I$_1$ (123) 20-(2,2-dimethylpropylidine)-9(O)-methano-$\Delta^{6(9\alpha)}$-prostaglandin I$_1$ (124) 20-propylidine-19,19-dimethyl-9(O)-methano-$\Delta^{6(9\alpha)}$-prostaglandin I$_1$ (125) 20-butylidine-9(O)-methano-$\Delta^{6(9\alpha)}$-prostaglandin I$_1$ (126) 20-butylidine-18-methyl-9(O)-methano-$\Delta^{6(9\alpha)}$-prostaglandin I$_1$ (127) 20-butylidine-18,18-dimethyl-9(O)-methano-$\Delta^{6(9\alpha)}$-prostaglandin I$_1$ (128) 20-butylidine-18,18-dimethyl-9(O)-methano-$\Delta^{6(9\alpha)}$-prostaglandin I$_1$ (129) 20-butylidine-19,19-dimethyl-9(O)-methano-$\Delta^{6(9\alpha)}$-prostaglandin I$_1$ (130) 20-butylidine-19-methyl-9(O)-methano-$\Delta^{6(9\alpha)}$-prostaglandin I$_1$ (131) 20-(2-methylbutylidine)-9(O)-methano-$\Delta^{6(9\alpha)}$-prostaglandin I$_1$ (132) 20-(2-ethylbutylidine)-9(O)-methano-$\Delta^{6(9\alpha)}$-prostaglandin I$_1$ (133) 20-(3-methylbutylidine)-9(O)-methano-$\Delta^{6(9\alpha)}$-prostaglandin I$_1$ (134) 20-(3,3-dimethylbutylidine)-9(O)-methano-$\Delta^{6(9\alpha)}$-prostaglandin I$_1$ (135) 20-(3,3-dimethylbutylidine)-9(O)-methano-$\Delta^{6(9\alpha)}$-prostaglandin I$_1$ (136) 20-ethynyl-9(O)-methano-$\Delta^{6(9\alpha)}$-prostaglandin I$_1$ (137) 20-ethynyl-18-methyl-9(O)-methano-$\Delta^{6(9\alpha)}$-prostaglandin I$_1$ (138) 20-ethynyl-19-methyl-9(O)-methano-$\Delta^{6(9\alpha)}$-prostaglandin I$_1$ (139) 20-ethynyl-19,19-dimethyl-9(O)-methano-$\Delta^{6(9\alpha)}$-prostaglandin I$_1$ (140) 20-ethynyl-20-methyl-9(O)-methano-$\Delta^{6(9\alpha)}$-prostaglandin I$_1$ (141) 20-ethynyl-20,20-trimethyl-9(O)-methano-$\Delta^{6(9\alpha)}$-prostaglandin I$_1$ (142) 20-(1-propynyl)-9(O)-methano-$\Delta^{6(9\alpha)}$-prostaglandin I$_1$ (143) 20-(1-propynyl)-18-methyl-9(O)-methano-$\Delta^{6(9\alpha)}$-prostaglandin I$_1$ (144) 20-(1-propynyl)-19-methyl-9(O)-methano-$\Delta^{6(9\alpha)}$-prostaglandin I$_1$ (145) 20-(1-propynyl)-19,19-dimethyl-9(O)-methano-$\Delta^{6(9\alpha)}$-prostaglandin I$_1$ (146) 20-(1-propynyl)-20-methyl-9(O)-methano-$\Delta^{6(9\alpha)}$-prostaglandin I$_1$ (147) 20-(1-propynyl)-20,20-dimethyl-9(O)-methano-$\Delta^{6(9\alpha)}$-prostaglandin I$_1$ (148) 20-(1-butynyl)-9(O)-methano-$\Delta^{6(9\Delta)}$-prostaglandin I$_1$ (149) 20-(1-butynyl)-18-methyl-9(O)-methano-$\Delta^{6(9\alpha)}$-prostaglandin I$_1$ (150) 20-(1-butynyl)-19-methyl-9(O)-methano-$\Delta^{6(9\alpha)}$-prostaglandin I$_1$ (151) 20-(1-butynyl)-19,19-dimethyl-9(O)-methano-$\Delta^{6(9\alpha)}$-prostaglandin I$_1$ (152) 20-(1-butynyl)-20-methyl-9(O)-methano-$\Delta^{6(9\alpha)}$-prostaglandin I$_1$ (153) 20-(3-methyl-1-butynyl)-9(O)-methano-$\Delta^{6(9\alpha)}$-prostaglandin I$_1$ (154) 20-(3,3-dimethyl-1-butynyl)-9(O)-methano-$\Delta^{6(9\alpha)}$-prostaglandin I$_1$ (155) 20-(2-butynyl)-9(O)-methano-$\Delta^{6(9\alpha)}$-prostaglandin I$_1$ (156) 20-(2-propynyl)-18-methyl-9(O)-methano-$\Delta^{6(9\alpha)}$-prostaglandin I$_1$ (157) 20-(2-propynyl)-18,18-dimethyl-9(O)-methano-$\Delta^{6(9\alpha)}$-prostaglandin I$_1$ (158) 20-(2-propynyl)-19-methyl-9(O)-methano-$\Delta^{6(9\alpha)}$-prostaglandin I$_1$ (159) 20-(2-propynyl)-19,19-dimethyl-9(O)-methano-$\Delta^{6(9\alpha)}$-prostaglandin I$_1$ (160) 20-(2-propynyl)-20-methyl-9(O)-methano-$\Delta^{6(9\alpha)}$-prostaglandin I$_1$ (161) 20-(1-methyl-2-propynyl)-9(O)-methano-$\Delta^{6(9\alpha)}$-prostaglandin I$_1$ (162) 20-(1,1-dimethyl-2-propynyl)-9(O)-methano-$\Delta^{6(9\alpha)}$-prostaglandin I$_1$ (163) 20-(2-butynyl)-9(O)-methano-$\Delta^{6(9\alpha)}$-prostaglandin I$_1$ (164) 20-(2-butynyl)-18-methyl-9(O)-methano-$\Delta^{6(9\alpha)}$-prostaglandin I$_1$ (165) 20-(2-butynyl)-18,18-dimethyl-9(O)-methano-$\Delta^{6(9\alpha)}$-prostaglandin I$_1$ (166) 20-(2-butynyl)-19,19-dimethyl-9(O)-methano-$\Delta^{6(9\alpha)}$-prostaglandin I$_1$ (167) 20-(2-butynyl)-20,20-dimethyl-9(O)-methano-$\Delta^{6(9\alpha)}$-prostaglandin I$_1$ (168) 20-(1-methyl-2-butynyl)-9(O)-methano-$\Delta^{6(9\alpha)}$-prostaglandin I$_1$ (169) 20-(1,1-dimethyl-2-butynyl)-9(O)-methano-$\Delta^{6(9\alpha)}$-prostaglandin I$_1$ (170) 20-(3-butynyl)-9(O)-methano-$\Delta^{6(9\alpha)}$-prostaglandin I$_1$ (171) 20-(3-butynyl)-18-methyl-9(O)-methano-$\Delta^{6(9\alpha)}$-prostaglandin I$_1$ (172) 20-(3-butynyl)-18,18-dimethyl-9(O)-methano-$\Delta^{6(9\alpha)}$-prostaglandin I$_1$ (173) 20-(3-butynyl)-20-methyl-9(O)-methano-$\Delta^{6(9\alpha)}$-prostaglandin I$_1$ (174) 20-(1-methyl-3-butynyl)-9(O)-methano-$\Delta^{6(9\alpha)}$-prostaglandin I$_1$ (175) 20-(2-methyl-3-butynyl)-9(O)-methano-$\Delta^{6(9\alpha)}$-prostaglandin I$_1$ (176) 20-(2,2-dimethyl-3-butynyl)-9(O)-methano-$\Delta^{6(9\alpha)}$-prostaglandin I$_1$ (177) 20-(1,1-dimethyl-3-butynyl)-9(O)-methano-$\Delta^{6(9\alpha)}$-prostaglandin I$_1$ (178) Methyl esters of (1) to (177)

(179) Ethyl esters of (1) to (177)

(180) Butyl esters of (1) to (177)

(181) Sodium salts of (1) to (177)

(182) Potassium salts of (1) to (177)

(183) Ammonium salts of (1) to (177)

Other preferable examples of the isocarbacyclin used in the present invention are as follows:

(201) 7-methyl-9(O)-methano-$\Delta^{6(9\alpha)}$-prostaglandin $I_1$ (202) 17(R),20-dimethyl-9(O)-methano-$\Delta^{6(9\alpha)}$-prostaglandin $I_1$ (203) 17(S),20-dimethyl-9(O)-methano-$\Delta^{6(9\alpha)}$-prostaglandin $I_1$ (204) 20-nol-17-methyl-9(O)-methano-$\Delta^{6(9\alpha)}$-prostaglandin $I_1$ (205) 17,19-dimethyl-9(O)-methano-$\Delta^{6(9\alpha)}$-prostaglandin $I_1$ (206) 17,18-dimethyl-9(O)-methano-$\Delta^{6(9\alpha)}$-prostaglandin $I_1$ (207) 17-methyl-20-ethyl-9(O)-methano-$\Delta^{6(9\alpha)}$-prostaglandin $I_1$ (208) 17-methyl-20-iso-propyl-9(O)-methano-$\Delta^{6(9\alpha)}$-prostaglandin $I_1$ (209) 17,20-dimethyl-20-ethyl-9(O)-methano-$\Delta^{6(9\alpha)}$-prostaglandin $I_1$ (210) 17,19-dimethyl-20-ethyl-9(O)-methano-$\Delta^{6(9\alpha)}$-prostaglandin $I_1$ (211) 17,18-dimethyl-20-ethyl-9(O)-methano-$\Delta^{6(9\alpha)}$-prostaglandin $I_1$ (212) 17-methyl-20-propyl-9(O)-methano-$\Delta^{6(9\alpha)}$-prostaglandin $I_1$ (213) 17,22-dimethyl-20-propyl-9(O)-methano-$\Delta^{6(9\alpha)}$-prostaglandin $I_1$ (214) 17,21-dimethyl-20-propyl-9(O)-methano-$\Delta^{6(9\alpha)}$-prostaglandin $I_1$ (215) 7,20-dimethyl-20-propyl-9(O)-methano-$\Delta^{6(9\alpha)}$-prostaglandin $I_1$ (216) 17,19-dimethyl-20-propyl-9(O)-methano-$\Delta^{6(9\alpha)}$-prostaglandin $I_1$ (217) 17,18-dimethyl-20-propyl-9(O)-methano-$\Delta^{6(9\alpha)}$-prostaglandin $I_1$ (218) 20-nol-17-methyl-18-methylene-9(O)-methano-$\Delta^{6(9\alpha)}$-prostaglandin $I_1$ (219) 20-nol-18,19-dehydro-17-methyl-9(O)-methano-$\Delta^{6(9\alpha)}$-prostaglandin $I_1$ (220) 18,19-dehydro-17-methyl-9(O)-methano-$\Delta^{6(9\alpha)}$-prostaglandin $I_1$ (221) 18,19-dehydro-17,20-dimethyl-9(O)-methano-$\Delta^{6(9\alpha)}$-prostaglandin $I_1$ (222) 18,19-dehydro-20-ethyl-17-methyl-9(O)-methano-$\Delta^{6(9\alpha)}$-prostaglandin $I_1$ (223) 18,19-dehydro-20-propyl-17-methyl-9(O)-methano-$\Delta^{6(9\alpha)}$-prostaglandin $I_1$ (224) 18,19-dehydro-20-butyl-17-methyl-9(O)-methano-$\Delta^{6(9\alpha)}$-prostaglandin $I_1$ (225) 18-methylene-17,20-dimethyl-9(O)-methano-$\Delta^{6(9\alpha)}$-prostaglandin $I_1$ (226) 18,19-dehydro-17,20,20-trimethyl-9(O)-methano-$\Delta^{6(9\alpha)}$-prostaglandin $I_1$ (227) 18,19-dehydro-17,20-dimethyl-20-ethyl-9(O)-methano-$\Delta^{6(9\alpha)}$-prostaglandin $I_1$ (228) 18,19-dehydro-20-isopropyl-17-methyl-20-ethyl-9(O)-methano-$\Delta^{6(9\alpha)}$-prostaglandin $I_1$ (229) 18,19-dehydro-17,20-dimethyl-20-butyl-9(O)-methano-$\Delta^{6(9\alpha)}$-prostaglandin $I_1$ (230) 18,19-dehydro-17-methyl-20-(1-methylpropyl)-9(O)-methano-$\Delta^{6(9\alpha)}$-prostaglandin $I_1$ (231) 18,19-dehydro-17,20-dimethyl-20-propyl-9(O)-methano-$\Delta^{6(9\alpha)}$-prostaglandin $I_1$ (232) 18,19-dehydro-17,20,20-trimethyl-20-butyl-9(O)-methano-$\Delta^{6(9\alpha)}$-prostaglandin $I_1$ (233) 19,20-dehydro-17-methyl-9(O)-methano-$\Delta^{6(9\alpha)}$-prostaglandin $I_1$ (234) 19,20-dehydro-17,20-dimethyl-9(O)-methano-$\Delta^{6(9\alpha)}$-prostaglandin $I_1$ (235) 19,20-dehydro-17,19-dimethyl-9(O)-methano-$\Delta^{6(9\alpha)}$-prostaglandin $I_1$ (236) 19,20-dehydro-17-methyl-20-ethyl-9(O)-methano-$\Delta^{6(9\alpha)}$-prostaglandin $I_1$ (237) 19,20-dehydro-17-methyl-20-propyl-9(O)-methano-$\Delta^{6(9\alpha)}$-prostaglandin $I_1$ (238) 19,20-dehydro-17-methyl-20-butyl-9(O)-methano-$\Delta^{6(9\alpha)}$-prostaglandin $I_1$ (239) 19,20-dehydro-17,18,20-trimethyl-9(O)-methano-$\Delta^{6(9\alpha)}$-prostaglandin $I_1$ (240) 19,20-dehydro-17-methyl-20-(1-methylpropyl)-9(O)-methano-$\Delta^{6(9\alpha)}$-prostaglandin $I_1$ (241) 19,20-dehydro-17-methyl-20-isopropyl-9(O)-methano-$\Delta^{6(9\alpha)}$-prostaglandin $I_1$ (242) 19,20-dehydro-17-methyl-20-(2-methylbutyl)-9(O)-methano-$\Delta^{6(9\alpha)}$-prostaglandin $I_1$ (243) 19,20-dehydro-17-methyl-20-(1,1-dimethylpropyl)-9(O)-methano-$\Delta^{6(9\alpha)}$-prostaglandin $I_1$ (244) 17-methyl-20-methylene-9(O)-methano-$\Delta^{6(9\alpha)}$-prostaglandin $I_1$ (245) 17,20-dimethyl-20-methylene-9(O)-methano-$\Delta^{6(9\alpha)}$-prostaglandin $I_1$ (246) 17,19-dimethyl-20-methylene-9(O)-methano-$\Delta^{6(9\alpha)}$-prostaglandin $I_1$ (247) 17-methyl-20-ethylidene-9(O)-methano-$\Delta^{6(9\alpha)}$-prostaglandin $I_1$ (248) 17-methyl-20-propylidene-9(O)-methano-$\Delta^{6(9\alpha)}$-prostaglandin $I_1$ (249) 17-methyl-20-butylidene-9(O)-methano-$\Delta^{6(9\alpha)}$-prostaglandin $I_1$ (250) 17-methyl-20-(1-ethylbutylidene)-9(O)-methano-$\Delta^{6(9\alpha)}$-prostaglandin $I_1$ (251) 17-methyl-20-(1-methylbutylidene)-9(O)-methano-$\Delta^{6(9\alpha)}$-prostaglandin $I_1$ (252) 17-methyl-20-(1-methylethylidene)-9(O)-methano-$\Delta^{6(9\alpha)}$-prostaglandin $I_1$ (253) 17,19-dimethyl-20-propylidene-9(O)-methano-$\Delta^{6(9\alpha)}$-prostaglandin $I_1$ (254) 17-methyl-20-(2-methylpropylidene)-9(O)-methano-$\Delta^{6(9\alpha)}$-prostaglandin $I_1$ (255) 17,19-dimethyl-20-butylidene-9(O)-methano-$\Delta^{6(9\alpha)}$-prostaglandin $I_1$ (256) 17-methyl-20-(3-methylbutylidene)-9(O)-methano-$\Delta^{6(9\alpha)}$-prostaglandin $I_1$ (257) 17,19,19-trimethyl-20-methylene-9(O)-methano-$\Delta^{6(9\alpha)}$-prostaglandin $I_1$ (258) 17-methyl-20-vinyl-9(O)-methano-$\Delta^{6(9\alpha)}$-prostaglandin $I_1$ (259) 17,19-dimethyl-20-vinyl-9(O)-methano-$\Delta^{6(9\alpha)}$-prostaglandin $I_1$ (260) 17,19,19-trimethyl-20-vinyl-9(O)-methano-$\Delta^{6(9\alpha)}$-prostaglandin $I_1$ (261) 17,20-dimethyl-20-vinyl-9(O)-methano-$\Delta^{6(9\alpha)}$-prostaglandin $I_1$ (262) 17-methyl-20-(1-methylvinyl)-9(O)-methano-$\Delta^{6(9\alpha)}$-prostaglandin $I_1$ (263) 17-methyl-20-(1-propenyl)-9(O)-methano-$\Delta^{6(9)\alpha}$-prostaglandin $I_1$ (264) 17-methyl-20-(2-methyl-1-propenyl)-9(O)-methano-$\Delta^{6(9)\alpha}$-prostaglandin $I_1$ (265) 17,19-dimethyl-20-(1-propenyl)-9(O)-methano-$\Delta^{6(9\alpha)}$-prostaglandin $I_1$ (266) 17,19,19-trimethyl-20-(1-propenyl)-9(O)-methano-$\Delta^{6(9)\alpha}$-prostaglandin $I_1$ (267) 17,19-dimethyl-20-(2-methyl-1-propenyl)-9(O)-methano-$\Delta^{6(9)\alpha}$-prostaglandin $I_1$ (268) 17,18-dimethyl-20-(2-methyl-1-propenyl)-9(O)-methano-$\Delta^{6(9)\alpha}$-prostaglandin $I_1$ (269) 17,18,18-trimethyl-20-(2-methyl-1-propenyl)-9(O)-methano-$\Delta^{6(9)\alpha}$-prostaglandin $I_1$ (270) 17-methyl-20-(1-butenyl)-9(O)-methano-$\Delta^{6(9)\alpha}$-prostaglandin $I_1$ (271) 17-methyl-20-(2-methyl-1-butenyl)-9(O)-methano-$\Delta^{6(9)\alpha}$-prostaglandin $I_1$ (272) 17-methyl-20-(2-ethyl-1-butenyl)-9(O)-methano-$\Delta^{6(9)\alpha}$-prostaglandin $I_1$ (273) 17,20-dimethyl-20-butenyl-9(O)-methano-$\Delta^{6(9)\alpha}$-prostaglandin $I_1$ (274) 17,19-dimethyl-20-butenyl-9(O)-methano-$\Delta^{6(9)\alpha}$-prostaglandin $I_1$ (275) 17,19,19-trimethyl-20-butenyl-9(O)-methano-$\Delta^{6(9\alpha)}$-prostaglandin $I_1$ (276) 20-nol-18,19-tetradehydro-17-methyl-9(O)-methano-$\Delta^{6(9)\alpha}$-prostaglandin $I_1$ (277) 18,19-tetradehydro-17-methyl-9(O)-methano-$\Delta^{6(9\alpha)}$-prostaglandin $I_1$ (278) 18,19-tetradehydro-17,20-dimethyl-9(O)-methano-$\Delta^{6(9)\alpha}$-prostaglandin $I_1$ (279) 18,19-tetradehydro-17-methyl-20-ethyl-9(O)-methano-$\Delta^{6(9)\alpha}$-prostaglandin $I_1$ (280) 18,19-tetradehydro-17-methyl-20-butyl-9(O)-methano-$\Delta^{6(9)\alpha}$-prostaglandin $I_1$ (281) 18,19-tetradehydro-17-methyl-20-propyl-9(O)-methano-$\Delta^{6(9)\alpha}$-prostaglandin $I_1$ (282) 18,19-tetradehydro-17,20,20-trimethyl-9(O)-methano-$\Delta^{6(9)\alpha}$-prostaglandin $I_1$ (283) 18,19-tetradehydro-17,20,20,20-tetramethyl-9(O)-methano-$\Delta^{6(9)\alpha}$-prostaglandin $I_1$ (284) 18,19-tetradehydro-17,20-dimethyl-20-ethyl-9(O)-methano-$\Delta^{6(9)\alpha}$-prostaglandin $I_1$ (285) 18,19-tetradehydro-17,20,20-trimethyl-20-ethyl-9(O)-methano-$\Delta^{6(9)\alpha}$-prostaglandin $I_1$ (286) 18,19-tetradehydro-17-methyl-20,20-diethyl-9(O)-methano-$\Delta^{6(9)\alpha}$-prostaglandin $I_1$ (287) 18,19-tetradehydro-17-methyl-20-isopropyl-9(O)-methano-$\Delta^{6(9)\alpha}$-prostaglandin $I_1$ (288) 18,19-tetradehydro-17-methyl-20-t-butyl-9(O)-methano-$\Delta^{6(9)\alpha}$-prostaglandin $I_1$ (289) 18,19-tetradehydro-17,20-dimethyl-20-propyl-9(O)-methano-$\Delta^{6(9)\alpha}$-prostaglandin $I_1$ (290) 18,19-tetradehydro-17,20,20-trimethyl-20-propyl-9(O)-methano-$\Delta^{6(9)\alpha}$-prostaglandin $I_1$ (291) 18,19-tetradehydro-17-methyl-20-(2-methylpropyl)-9(O)-methano-$\Delta^{6(9)\alpha}$-prostaglandin $I_1$ (292) 18,19-tetradehydro-17-methyl-20-(2,2-dimethylpropyl)-9(O)-methano-$\Delta^{6(9)\alpha}$-prostaglandin $I_1$ (293) 18,19-tetradehydro-17,20-dimethyl-20-butyl-9(O)-methano-$\Delta^{6(9)\alpha}$-prostaglandin $I_1$ (294) 18,19-tetradehydro-17,20,20-trimethyl-20-butyl-9(O)-methano-$\Delta^{6(9)\alpha}$-prostaglandin $I_1$ (295) 18,19-tetradehydro-17-methyl-20-(2-methylbutyl)-9(O)-methano-$\Delta^{6(9)\alpha}$-prostaglandin $I_1$ (296) 18,19-tetradehydro-17-methyl-20-(2-ethylbutyl)-9(O)-methano-$\Delta^{6(9)\alpha}$-prostaglandin $I_1$ (297) 18,19-tetradehydro-17-methyl-20-(2,2-dimethylbutyl)-9(O)-methano-$\Delta^{6(9)\alpha}$-prostaglandin $I_1$ (298) 19,20-tetradehydro-17-methyl-9(O)-methano-$\Delta^{6(9\alpha)}$-prostaglandin $I_1$ (299) 19,20-tetradehydro-17,18-dimethyl-9(O)-methano-$\Delta^{6(9)\alpha}$-prostaglandin $I_1$ (300) 19,20-tetradehydro-17,18,20-trimethyl-9(O)-methano-$\Delta^{6(9)\alpha}$-prostaglandin $I_1$ (301) 19,20-tetradehydro-17,20-dimethyl-9(O)-methano-$\Delta^{6(9)\alpha}$-prostaglandin $I_1$ (302) 19,20-tetradehydro-17-methyl-20-ethyl-9(O)-methano-$\Delta^{6(9)\alpha}$-prostaglandin $I_1$ (303) 19,20-tetradehydro-17-methyl-20-isopropyl-9(O)-methano-$\Delta^{6(9)\alpha}$-prostaglandin $I_1$ (304) 19,20-tetradehydro-17-methyl-20-t-butyl-9(O)-methano-$\Delta^{6(9)\alpha}$-prostaglandin $I_1$ (305) 19,20-tetradehydro-17-methyl-20-propyl-9(O)-methano-$\Delta^{6(9)\alpha}$-prostaglandin $I_1$ (306) 19,20-tetradehydro-17-methyl-20-(1-methylpropyl)-9(O)-methano-$\Delta^{6(9)\alpha}$-prostaglandin $I_1$ (307) 19,20-tetradehydro-17-methyl-20-(1-ethylpropyl)-9(O)-methano-$\Delta^{6(9)\alpha}$-prostaglandin $I_1$ (308) 19,20-tetradehydro-17-methyl-20-(1,1-dimethylpropyl)-9(O)-methano-$\Delta^{6(9)\alpha}$-prostaglandin $I_1$ (309) 19,20-tetradehydro-17-methyl-20-butyl-9(O)-methano-$\Delta^{6(9)\alpha}$-prostaglandin $I_1$ (310) 19,20-tetradehydro-17,18-dimethyl-20-butyl-9(O)-methano-$\Delta^{6(9)\alpha}$-prostaglandin $I_1$ (311) 19,20-tetradehydro-17-methyl-20-(1-methylbutyl)-9(O)-methano-$\Delta^{6(9)\alpha}$-prostaglandin $I_1$ (312) 19,20-tetradehydro-17-methyl-20-(1,1-dimethylbutyl)-9(O)-methano-$\Delta^{6(9)\alpha}$-prostaglandin $I_1$ (313) 19,20-tetradehydro-17-methyl-20-(2,2-dimethylbutyl)-9(O)-methano-$\Delta^{6(9)\alpha}$-prostaglandin $I_1$ (314) 19,20-tetradehydro-17-methyl-20-(2-ethylbutyl)-9(O)-methano-$\Delta^{6(9)\alpha}$-prostaglandin $I_1$ (315) 19,20-tetradehydro-17,18-dimethyl-20-propyl-9(O)-methano-$\Delta^{6(9)\alpha}$-prostaglandin $I_1$ (316) 20-methylidine-17-methyl-9(O)-methano-$\Delta^{6(9)\alpha}$-prostaglandin $I_1$ (317) 20-methylidine-17,18-dimethyl-9(O)-methano-$\Delta^{6(9\alpha)}$-prostaglandin $I_1$ (318) 20-methylidine-17,20-dimethyl-9(O)-methano-$\Delta^{6(9\alpha)}$-prostaglandin $I_1$ (319) 20-ethylidine-17-methyl-9(O)-methano-$\Delta^{6(9)\alpha}$-prostaglandin $I_1$ (320) 20-propylidine-17-methyl-9(O)-methano-$\Delta^{6(9)\alpha}$-prostaglandin $I_1$ (321) 20-(2-methylpropylidine)-17-methyl-9(O)-methano-$\Delta^{6(9)\alpha}$-prostaglandin $I_1$ (322) 20-propylidine-17,19-dimethyl-9(O)-methano-$\Delta^{6(9\alpha)}$-prostaglandin $I_1$ (323) 20-(2,2-dimethylpropylidine)-17-methyl-9(O)-methano-$\Delta^{6(9)\alpha}$-prostaglandin $I_1$ (324) 20-propylidine-17,19,19-trimethyl-9(O)-methano-$\Delta^{6(9)\alpha}$-prostaglandin $I_1$ (325) 20-butylidine-17-methyl-9(O)-methano-$\Delta^{6(9\alpha)}$-prostaglandin $I_1$ (326) 20-butylidine-17,18-dimethyl-9(O)-methano-$\Delta^{6(9\alpha)}$-prostaglandin $I_1$ (327) 20-butylidine-17,18,18-trimethyl-9(O)-methano-$\Delta^{6(9\alpha)}$-prostaglandin $I_1$ (328) 20-butylidine-17,18,18-trimethyl-9(O)-methano-$\Delta^{6(9\alpha)}$-prostaglandin $I_1$ (329) 20-butylidine-17,19,19-trimethyl-9(O)-methano-$\Delta^{6(9\alpha)}$-prostaglandin $I_1$ (330) 20-butylidine-17,19-dimethyl-9(O)-methano-$\Delta^{6(9\alpha)}$-prostaglandin $I_1$ (331) 20-(2-methylbutylidine)-17-methyl-9(O)-methano-$\Delta^{6(9\alpha)}$-prostaglandin $I_1$ (332) 20-(2-ethylbutylidine)-17-methyl-9(O)-methano-$\Delta^{6(9\alpha)}$-prostaglandin $I_1$ (333) 20-(3-methylbutylidine)-17-methyl-9(O)-methano-$\Delta^{6(9\alpha)}$-prostaglandin $I_1$ (334) 20-(3,3-dimethylbutylidine)-17-methyl-9(O)-methano-$\Delta^{6(9\alpha)}$-prostaglandin $I_1$ (335) 20-(3,3-dimethylbutylidine)-17-methyl-9(O)-methano-$\Delta^{6(9\alpha)}$-prostaglandin $I_1$ (336) 20-ethynyl-17-methyl-9(O)-methano-$\Delta^{6(9\alpha)}$-prostaglandin $I_1$ (337) 20-ethynyl-17,18-dimethyl-9(O)-methano-$\Delta^{6(9\alpha)}$-prostaglandin $I_1$ (338) 20-ethynyl-17,19-dimethyl-9(O)-methano-$\Delta^{6(9\alpha)}$-prostaglandin $I_1$ (339) 20-ethynyl-17,19,19-trimethyl-9(O)-methano-$\Delta^{6(9\alpha)}$-prostaglandin $I_1$ (340) 20-ethynyl-17,20-dimethyl-9(O)-methano-$\Delta^{6(9\alpha)}$-prostaglandin $I_1$ (341) 20-ethynyl-17,20,20-trimethyl-9(O)-methano-$\Delta^{6(9\alpha)}$-prostaglandin $I_1$ (342) 20-(1-propynyl)-17-methyl-9(O)-methano-$\Delta^{6(9\alpha)}$-prostaglandin $I_1$ (343) 20-(1-propynyl)-17,18-dimethyl-9(O)-methano-$\Delta^{6(9\alpha)}$-prostaglandin $I_1$ (344) 20-(1-propynyl)-17,19-dimethyl-9(O)-methano-$\Delta^{6(9\alpha)}$-prostaglandin $I_1$ (345) 20-(1-propynyl)-17,19,19-trimethyl-9(O)-methano-$\Delta^{6(9\alpha)}$-prostaglandin $I_1$ (346) 20-(1-propynyl)-17,20-dimethyl-9(O)-methano-$\Delta^{6(9\alpha)}$-prostaglandin $I_1$ (347) 20-(1-propynyl)-17,20,20-trimethyl-9(O)-methano-$\Delta^{6(9\alpha)}$-prostaglandin $I_1$ (348) 20-(1-butynyl)-17-methyl-9(O)-methano-$\Delta^{6(9\alpha)}$-prostaglandin $I_1$ (349) 20-(1-butynyl)-17,18-dimethyl-9(O)-methano-$\Delta^{6(9\alpha)}$-prostaglandin $I_1$ (350) 20-(1-butynyl)-17,19-dimethyl-9(O)-methano-$\Delta^{6(9\alpha)}$-prostaglandin $I_1$ (351) 20-(1-butynyl)-17,19,19-trimethyl-9(O)-methano-$\Delta^{6(9\alpha)}$-prostaglandin $I_1$ (352) 20-(1-butynyl)-17,20-dimethyl-9(O)-methano-$\Delta^{6(9\alpha)}$-prostaglandin $I_1$ (353) 20-(3-methyl-1-butynyl)-17-methyl-9(O)-methano-$\Delta^{6(9\alpha)}$-prostaglandin $I_1$ (354) 20-(3,3-dimethyl-1-butynyl)-17-methyl-9(O)-methano-$\Delta^{6(9\alpha)}$-prostaglandin $I_1$ (355) 20-(2-butynyl)-17-methyl-9(O)-methano-$\Delta^{6(9\alpha)}$-prostaglandin $I_1$ (356) 20-(2-propynyl)-17,18-dimethyl-9(O)-methano-$\Delta^{6(9\alpha)}$-prostaglandin $I_1$ (357) 20-(2-propynyl)-17,18,18-trimethyl-9(O)-methano-$\Delta^{6(9\alpha)}$-prostaglandin $I_1$ (358) 20-(2-propynyl)-17,19-dimethyl-9(O)-methano-$\Delta^{6(9\alpha)}$-prostaglandin $I_1$ (359) 20-(2-propynyl)-17,19,19-trimethyl-9(O)-methano-$\Delta^{6(9\alpha)}$-prostaglandin $I_1$ (360) 20-(2-propynyl)-17,20-dimethyl-9(O)-methano-$\Delta^{6(9\alpha)}$-prostaglandin $I_1$ (361) 20-(1-methyl-2-propynyl)-17-methyl-9(O)-methano-$\Delta^{6(9\alpha)}$-prostaglandin $I_1$ (362) 20-(1,1-dimethyl-2-propynyl)-17-methyl-9(O)-methano-$\Delta^{6(9\alpha)}$-prostaglandin $I_1$ (363) 20-(2-butynyl)-17-methyl-9(O)-methano-$\Delta^{6(9\alpha)}$-prostaglandin $I_1$ (364) 20-(2-butynyl)-17,18-dimethyl-9(O)-methano-$\Delta^{6(9\alpha)}$-prostaglandin $I_1$ (365) 20-(2-butynyl)-17,18,18-trimethyl-9(O)-methano-$\Delta^{6(9\alpha)}$-prostaglandin $I_1$ (366) 20-(2-butynyl)-17,19,19-trimethyl-9(O)-methano-$\Delta^{6(9\alpha)}$-prostaglandin $I_1$ (367) 20-(2-butynyl)-17,20,20-trimethyl-9(O)-methano-$\Delta^{6(9\alpha)}$-prostaglandin $I_1$ (368) 20-(1-methyl-2-butynyl)-17-methyl-9(O)-methano-$\Delta^{6(9\alpha)}$-prostaglandin $I_1$ (369) 20-(1,1-dimethyl-2-butynyl)-17-methyl-9(O)-methano-$\Delta^{6(9\alpha)}$-prostaglandin $I_1$ (370) 20-(3-butynyl)-17-methyl-9(O)-methano-$\Delta^{6(9\alpha)}$-prostaglandin $I_1$ (371) 20-(3-butynyl)-17,18-dimethyl-9(O)-methano-$\Delta^{6(9\alpha)}$-prostaglandin $I_1$ (372) 20-(3-butynyl)-17,18,18-trimethyl-9(O)-methano-$\Delta^{6(9\alpha)}$-prostaglandin $I_1$ (373) 20-(3-butynyl)-17,20-dimethyl-9(O)-methano-$\Delta^{6(9\alpha)}$-prostaglandin $I_1$ (374) 20-(1-methyl-3-butynyl)-17-methyl-9(O)-methano-$\Delta^{6(9\alpha)}$-prostaglandin $I_1$ (375) 20-(2-methyl-3-butynyl)-17-methyl-9(O)-methano-$\Delta^{6(9\alpha)}$-prostaglandin $I_1$ (376) 20-(2,2-dimethyl-3-butynyl)-17-methyl-9(O)-methano-$\Delta^{6(9\alpha)}$-prostaglandin $I_1$ (377) 20-(1,1-dimethyl-3-butynyl)-17-methyl-9(O)-methano-$\Delta^{6(9\alpha)}$-prostaglandin $I_1$ (378) Methyl esters of (201) to (377)

(379) Ethyl esters of (201) to (377)

(380) Butyl esters of (201) to (377)

(381) Sodium salts of (201) to (377)

(382) Potassium salts of (201) to (377)

(383) Ammonium salts of (201) to (377)

(384) (201) to (383), of which the 17-position methyl group is replaced to ethyl, etc. may be mentioned, but the present invention is not limited to these examples.

Mentioning other preferable concrete-examples of the isocarbacyclin usable in the present invention, there are for example the following.

(401) 16,17,18,19,20-pentanol-15-cyclopentyl-9(O)-methano-$\Delta^{6(9\alpha)}$-prostaglandin $I_1$ (402) 16,17,18,19,20-pentanol-15-cyclohexyl-9(O)-methano-$\Delta^{6(9\alpha)}$-prostaglandin $I_1$ (403) 17-ethoxy-9(O)-methano-$\Delta^{6(9\alpha)}$-prostaglandin $I_1$ (404) 16,17,18,19,20-pentanol-15-(2-chlorocyclopentyl)-9(O)-methano-$\Delta^{6(9)\alpha)}$-prostaglandin $I_1$ (405) 16,17,18,19,20-pentanol-15-(3-trifluoromethylcyclohexyl)-9(O)-methano-$\Delta^{6(9)\alpha)}$-prostaglandin $I_1$ (406) Methyl esters of (401) to (405)

(407) t-Butyl esters of (401) to (405)

The isocarbacyclin having the above formula (1) may be easily produced by a known method. The method of production is described in detail, for example, in Japanese Unexamined Patent Publication (Kokai) No. 59-210044 and No. 61-197518 and in "Journal of Synthetic Organic Chemistry Japan" vol. 50, p. 143, 1992, etc.

The pharmaceutical composition for chronic arterial occlusion according to the present invention contains the isocarbacyclin having the formula (1) as an effective ingredient in a range of 0.2 to 1000 $\mu$g/ml. The composition according to the present invention also includes 0.05 to 0.5 g of a vegetable oil per ml of the composition, 0.01 to 0.5 g of a phospholipid per g of the vegetable oil, and a suitable amount of water. The phospholipids are preferably included in an amount of 0.05 to 0.3 g per g of the vegetable oil. As the vegetable oil usable in the present invention, for example, soybean oil may be mentioned. The soybean oil is preferably a high purity refined soybean oil, more particularly a high purity refined soybean oil obtained by further refining refined soybean oil by, for example, the steam distillation method (purity: containing at least 99.9% as triglyceride, diglyceride, and monoglyceride).

The phospholipid usable in the present invention is, for example, eggyolk lecithin, soybean lecithin, or other refined phospholipids and can be prepared by a usual method, that is, the fractionation method using an organic solvent. That is, for example, crude eggyolk phospholipids are dissolved in cold n-hexane-acetone, acetone is gradually added under stirring, the insolubles are collected by filtration, this operation is repeated once more, then the solvent is distilled off to obtain refined phospholipids. This is mainly consist of phosphatidylcholine and phosphatidylethanolamine. As other phospholipids, phosphatidylinositol, phosphatidylserine, sphingomyelins, etc. may be mentioned.

In the pharmaceutical composition of the present invention, if necessary, it is possible to add an emulsification adjuvant, stabilizer, high molecular isotonic agent, osmotic pressure adjuster, pH adjuster, etc.

As the emulsification adjuvant, there are for example $C_6$ to $C_{22}$, preferably $C_{12}$ to $C_{20}$ fatty acids or their physiologically usable salts etc. in an amount of up to 0.03 g per ml of the composition. These $C_6$ to $C_{22}$ fatty acids may be any fatty acids which may be added to pharmaceuticals. The fatty acid may be straight chained or branched. Stearic acid, oleic acid, linolic acid, palmic acid, linoleic acid, myristic acid of straight chain fatty acids, etc. are preferred. As these salts, a physiologically usable salt, for example, sodium salt, potassium salt, or other alkali metal salt, calcium salt or other alkali earth metal salt, etc. may be used.

As the stabilizer, there are for example a 0.005 g or less, preferably 0.001 g or less amount of cholesterol per ml of the composition or a 0.001 g or less amount of the phosphatidic acid etc.

The cholesterol or phosphatidic acid used may be any which may be used for a pharmaceutical.

As the high molecular isotonic agent, for example, there are albumin, dextran, vinyl polymer, an anionic surfactant, gelatin, hydroxyethyl starch, etc. in an amount of 0.1 to 5 parts by weight, preferably 0.5 to 1 parts by weight, per 1 part by weight of the isocarbacyclin.

As the albumin, vinyl polymer, and anionic surfactant, the following are preferred. That is, examples of the albumin are human-derived albumin due to the problem of antigenicity. As the vinyl polymer, polyvinyl pyrrolidone etc. may be mentioned. As the anionic surfactant, a polyalkylene glycol (for example polyethylene glycol of an average molecular weight of 1000 to 10000, preferably 4000 to 6000), a polyoxyalkylene copolymer (for example, a polyoxyethylene-polyoxypropylene copolymer of an average molecular weight of 1000 to 20000, preferably 6000 to 10000), a hardened castor oil polyoxyalkylene derivative (for example, hardened castor oil-polyoxyethylene-(40)-ether, same-(20)-ether, same-(100)-ether, etc.), a castor oil-polyoxyalkylene derivative (for example, castor oil polyoxyethylene-(20)-ether, same-(40)-ether, same-(100)-ether, etc. may be used.

As the osmotic pressure adjuster, glycerine etc. may be used. Further, as the pH adjuster, caustic soda etc. may be used.

The content of the isocarbacyclin in the composition may be suitably adjusted according to the form and application of the emulsion, but in general it is sufficient that if an extremely small amount, for example, 0.2 to 1000 $\mu$g/ml, more preferably 0.2 to 100 $\mu$g/ml, is contained in the composition.

The pharmaceutical composition in the form of the lipid emulsion according to the present invention is produced, for example, by the following method. That is, prescribed amounts of soybean oil, phospholipids, isocarbacyclin, and other additives are mixed and heated to make a solution which is then homogenized by an ordinary homogenizer, for example, pressurized injection type homogenizer, ultrasonic homogenizer, etc. then added with a necessary amount of water and again homogenized by the homogenizer to produce the composition of the present invention. Due to manufacturing concerns, it is possible after the production of the composition to add a stabilizer, isotonic agent, or other additive.

Further, the pharmaceutical composition in the form of a lipid emulsion according to the present invention has extreme fine particles of an average particle size of 1 $\mu$m or less and is extremely good in storage stability.

The pharmaceutical composition of the present invention may be administered by injection or other non-oral methods. Particularly intravenous administration is preferred. For example, the dosage may be 0.1 to 5 $\mu$g, preferably 0.5 to 3 $\mu$g, more preferably about 1 to 2 $\mu$g, per day per patient as isocarbacyclin content. This dosage may be administered once a day or divided into several times a day. In the intravenous administration of the medicine, it is preferable that the composition itself or one diluted by a suitable vehicle be administered by one shot injection or infusion. As the diluting vehicle etc., physiological saline, a glucose solution, a xylitol solution, Solita $T_3$, or other electrolyte solution, glycerol, etc. may be mentioned. The dilution rate is 0 to 1000 parts by weight per 1 part by weight of the present composition. As the method of administration of the present composition, for example, 1 part by weight of the present agent is preferably diluted with approximately 9 parts by weight of a diluent and administered once a day. The period of administration of the present composition is for example 1 day to 100 days, preferably 14 days to 35 days, particularly preferably about 28 days.

The pharmaceutical composition for chronic arterial occlusion of the present invention has a powerful action, a slow release, and lesion selectivity, so enables effective treatment in small dosages and has little side effects. Since the preparation has a powerful platelet aggregation suppressing action, vasodilation action, etc., it exhibits effects against various circulation disorders etc. Among these, in particular, it exhibits a remarkable effect against chronic arterial occlusion caused by the peripheral vessels closed by thrombus etc. and the peripheral circulation deteriorating. In chronic arterial occlusion, when the peripheral vessels are closed by thrombus etc. and the peripheral circulation deteriorates, the patient feels cold, numb and resting pain at their limbs, and suffers from intermittent claudication and ulcers. This preparation was found to have a remarkable effect of improving such disorders by improving the peripheral circulation obstructions.

EXAMPLES

The present invention will now be explained in further detail by Examples, but the present invention is not limited to these Examples.

Example 1

To 10 g of refined soybean oil were added 1.2 g of eggyolk lecithin and 100 $\mu$g of 9(O)-methano-$\Delta^{6(9)}\alpha$-prostaglandin $I_1$ methyl ester (isocarbacyclin methyl ester (methyl ester of above compound (1))). This was then heated to approximately 65 to 80° C. and mixed. To the resultant solution were added 50 ml of distilled water and then 2.2 g of glycerol. Further, distilled water was injected to bring the solution to 100 ml, then the solution was roughly emulsified by a homomixer. Next, it was further emulsified by passing it 11 times through a Manton-Gaulin homogenizer at a pressure of 530 kg/cm$^2$ to obtain a lipid emulsion containing 10% soybean oil with a final concentration of isocarbacyclin methyl ester of 1 $\mu$g/ml.

Example 2

According to the following method, a lipid emulsion of the isocarbacyclin methyl ester obtained in the same way as Example 1 was administered to chronic arterial occlusion patients.

Patients: Thromboangitis obliterans (TAO) or arteriosclerosis obliterans (ASO) patients having ischemic ulcers Test drug: 2 ml ampoules of lipid emulsion containing isocarbacyclin methyl ester in amounts of 1 $\mu$g, 2 $\mu$g, or 4 $\mu$g Test method: Double blind comparative-test using 3 groups Dosage: 1 $\mu$g/day, 2 $\mu$g/day, or 4 $\mu$g/day Method of administration: 1 ampoule per day was mixed in physiological saline to dilute to 10 ml and injected intravenously every day.

Period of administration: 4 weeks

Analyzed Examples: 155 examples

Method of evaluation: The degree of overall improvement was evaluated from the degree of improvement of the ischemic ulcer symptoms (size, condition of granulation, infection) and subjective symptoms (resting pain, coldness of limbs, or numbness). That is, four ranks of evaluation criteria were set for the condition of granulation, resting pain, coldness and numbness of limbs, and the symptoms before the start of administration of the drug and the symptoms after administration were compared. From the results, five rankings were given: remarkable, intermediate, light, no change, and deterioration. On the other hand, the size of the ulcers was judged by actual measurement of the diameters of the ulcers and the infection was judged by observation. These were similarly evaluated in five ranks.

The degree of overall improvement at the end of administration is shown in Table 1. The ratios of patients showing more than intermediate degrees of improvement at each dosage were 1 $\mu$g group: 61.7%, 2 $\mu$g group: 66.7%, and 4 $\mu$g group: 44.4%. The 2 $\mu$g group showed the largest value. Further, in main items of evaluation, which were the treatment of ischemic ulcers, rate of reduction of the ulcer diameter (FIG. 1), improvement of resting pain, and other, the 2 $\mu$g group showed a superior effect compared with other groups.

TABLE 1

Final Degree of Overall Improvement

| Dosage group | Remarkable improvement | Intermediate improvement | Light improvement | No change | Deterioration | Total | H-test Scheffé | Intermediate improvement or better | $X^2$ test Scheffé |
|---|---|---|---|---|---|---|---|---|---|
| 1 $\mu$g group | 10 (21.3) | 19 (40.4) | 8 (17.0) | 3 (6.4) | 7 (14.9) | 47 | N.S. | 29 (61.7) | $X^2$:p = 0.0809 |
| 2 $\mu$g group | 16 (35.6) | 14 (31.1) | 7 (15.6) | 3 (6.7) | 5 (11.1) | 45 | | 30 (66.7) | Scheffé: N.S. |
| 4 $\mu$g group | 8 (17.8) | 12 (26.7) | 14 (31.1) | 4 (8.9) | 7 (15.6) | 45 | | 20 (44.4) | |

(Note)
Figures in the table show number of patients. Figures in parentheses show percentages.

The degree of overall improvement of the 2 $\mu$g group by period after onset and by diameter of ulcer is shown in Table 2. An extremely high degree of overall improvement (intermediate improvement or better) of 79.3% of the patients in the case of less than one year after onset and ulcers of diameters of less than 25 mm was shown. Further, for the resting pain as well, a high degree of improvement of 60% was seen in the 2 $\mu$g group.

TABLE 2

Degree of Overall Improvement by Period
After Onset and by Size of Ulcers (Percentage of Patients With At Least Intermediate Improvement)

| Period after onset | | Diameter of ulcer | |
|---|---|---|---|
| Less than one year | 75.8% | Less than 25 mm | 70.3% |
| One year or more | 45.5% | 25 mm or more | 50.0% |

Further, for the cases where prostaglandin $E_1$ had no effect as well, in the 2 $\mu$g group, high values of 66.7% each were shown for the degree of overall improvement (intermediate improvement or better) and degree of improvement of the ulcer condition. Further, high degrees of improvement of 56.2% and 52.9% were shown for the resting pain and coldness as well. The overall degree of safety was shown in Table 3. The overall degree of safety is an indicator of safety giving consideration to the occurrence of side effects etc. as well. In the 2 μg group, safe or better was achieved by 96.1% and no serious side effects were observed either.

TABLE 3

Overall Safety

| Dosage group | Safe | Fairly safe | Problem in safety | Not safe | Total | H-test Scheﬁé | Safe or better | $X^2$-test Scheﬁé |
|---|---|---|---|---|---|---|---|---|
| 1 μg group | 45 (84.9) | 5 (9.4) | 3 (5.7) | 0 | 53 | N.S. | 45 (84.9) | N.S. |
| 2 μg group | 49 (96.1) | 2 (3.9) | 0 | 0 | 51 | | 49 (96.1) | |
| 4 μg group | 45 (88.2) | 4 (7.8) | 2 (3.9) | 0 | 51 | | 45 (88.2) | |

(Note)
Figures in the table show number of patients. Figures in parentheses show percentages.

Example 3

Using a lipid emulsion of isocarbacyclin methyl ester obtained in the same way as in Example 1, the effect on peripheral circulation disorders was evaluated by the generally used rat laurate-induced peripheral arterial occlusion model. Further, a comparison was made in this model with LipoPGE$_1$ which is a similar lipid preparation as the lipid emulsion of the present invention and is considered suitable for the same chronic arterial occlusion. Further, the used LipoPGE1 was one prepared in accordance with the method described in the examples of Japanese Unexamined Patent Publication (Kokai) No. 58-222014. For the rat laurate-induced peripheral arterial occlusion model, use was made of the following method by a modification of an known method (Ashida S. et al., Thromb, Res., 18, 55, 1980).

Rats (Wistar, male, 8 weeks old) were anesthesized by sodium pentobarbitol. For example, 150 μl or another predetermined amount of the lipid emulsion of the present invention or LipoPGE$_1$ was administered into the rat tail vein by one shot, then the femoral artery was immediately exposed and a part of it was peeled away. Ten minutes after administration of the lipid emulsion of the present invention (or LipoPGE$_1$), the heart side of the peeled femoral artery was ligated and 100 μl of sodium laurate (0.86 mg/leg) was injected into the femoral artery in the forward direction. The location of injection of sodium laurate was stopped from bleeding by an instant adhesive, then the ligation of the femoral artery was released and the epidermis was sutured. Starting the next day, 150 μl amounts of various concentrations of the lipid emulsion of the present invention (or LipoPGE$_1$) were administered once a day from the tail vein by one shot for 6 days. The efficacy of the lipid emulsion of the present invention was evaluated by scoring and evaluating every day the degree of disorder of the feet of rats injected with sodium laurate in accordance with the score table of Table 4.

TABLE 4

Score

For each digits,
0: normal appearance
1: change in nail color
2: change in digit color TABLE 4-continued Score 3: gangrene of digit
4: falling off or mummification of digit The sum of the grade for each digit was the score of the limb's lesion. Moreover, if the paw developed gangrene, a score of 5 was added to this sum and if the paw fell off or became mummified, a score of 10 was added to it.

Figure 2:
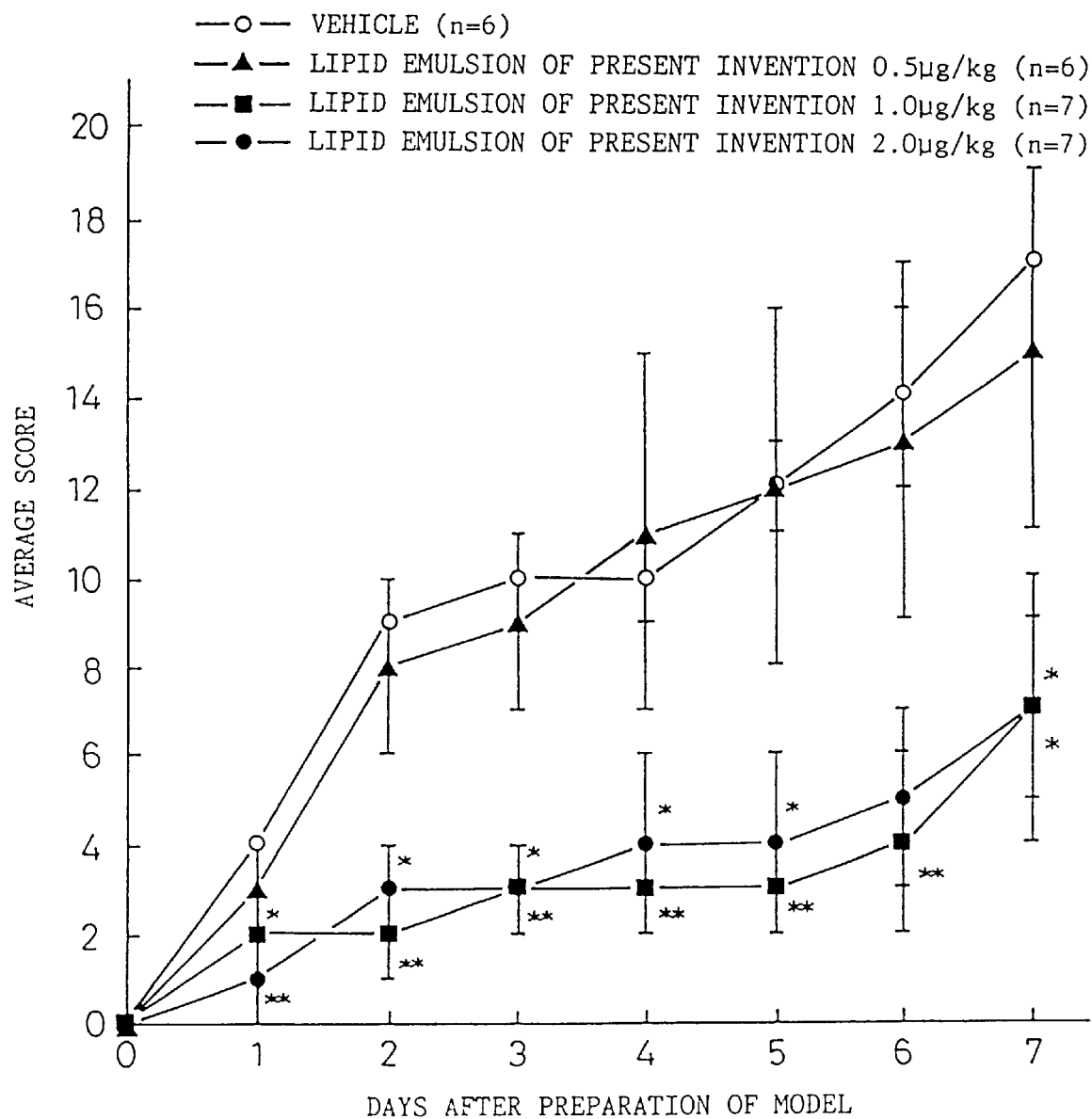
FIG. 2 is a view illustrating the efficacy when using the lipid emulsion of the present invention for rats with laurate-induced peripheral arterial occlusion.
Figure 3:
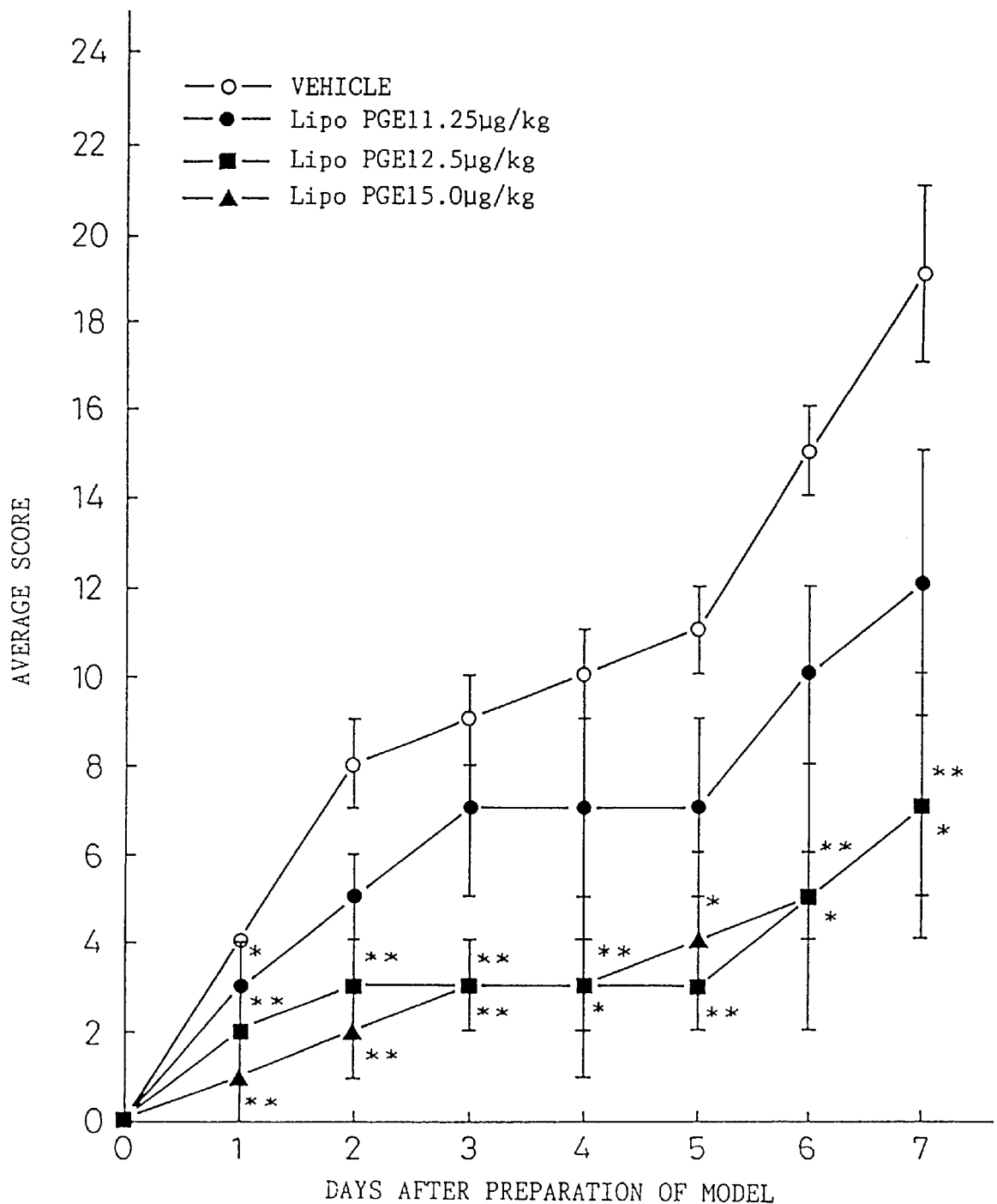
FIG. 3 is a view illustrating the efficacy when using $LipoPGE_1$ for rats with laurate-induced peripheral arterial occlusion.
Figure 4:
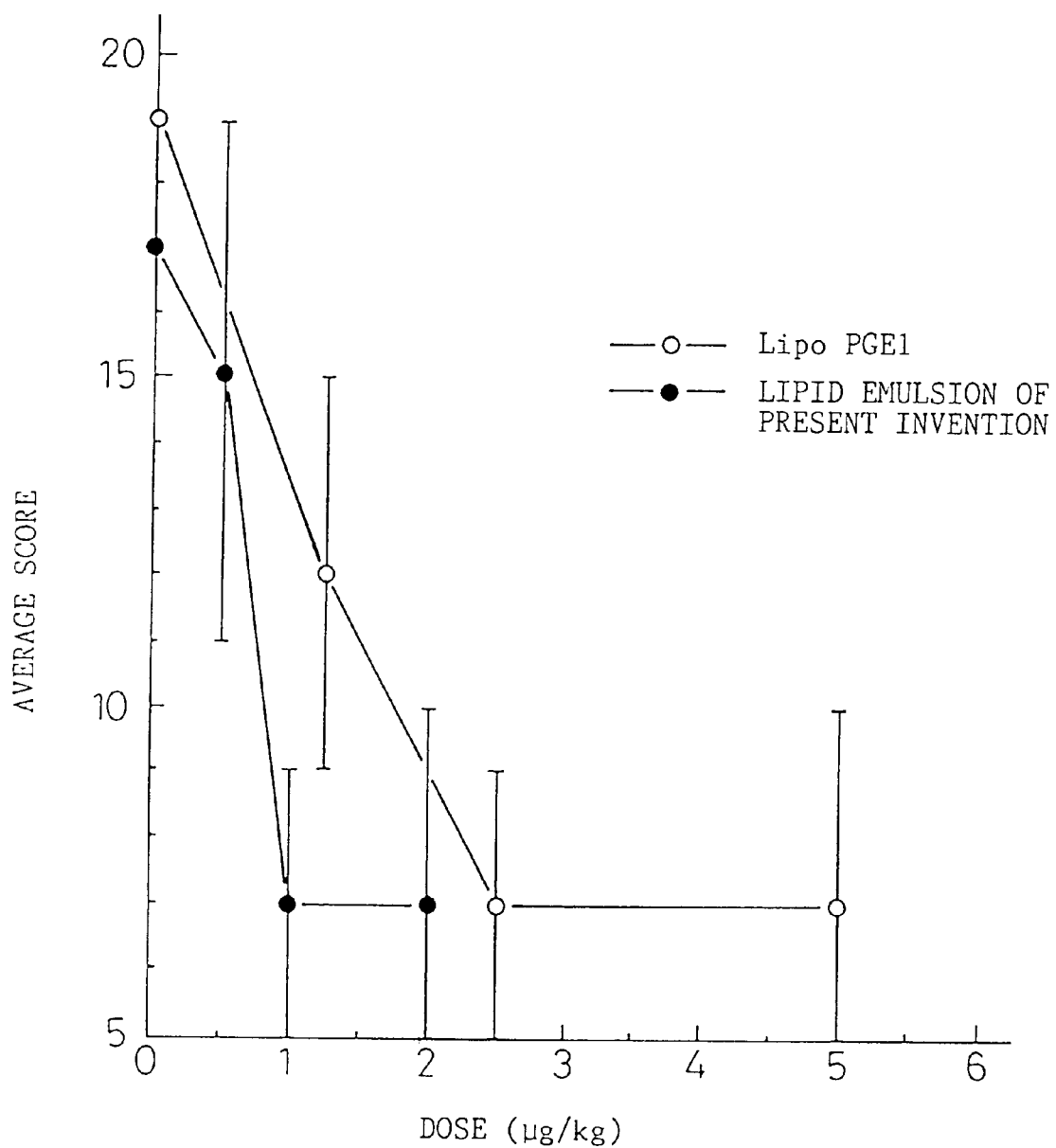
FIG. 4 is a view comparing the efficacies of the lipid emulsion of the present invention and Lipo PGE1 on rats with laurate-induced peripheral arterial occlusion.

The results of the evaluation of the lipid emulsion of the present invention and LipoPGE$_1$ in this model are shown in FIGS. 2 to 4. Further, in the same figure, for the vehicle of the lipid emulsion of the present invention or LipoPGE1, use was made of lipid emulsions not containing any active ingredients. FIG. 2 and FIG. 3 graph the daily changes of the average score ± standard error in the case of administration of various concentrations of the lipid emulsion of the present invention or LipoPGE$_1$. The statistical analysis was performed using the Mann-Whitney U-test and comparing with a vehicle group. Further, in FIG. 2 and FIG. 3, for the results of the statistical analysis, P<0.05 is shown by * and P<0.01 is shown by **. FIG. 4 compares the average score ± standard error of the lipid emulsion of the present invention and the LipoPGE1 group at day 7 after preparation of this model.

The following becomes clear from FIG. 2 to FIG. 4. LipoPGE$_1$ has a significant efficacy in dosages of 2.5 μg/kg or more and reproduces the published data (Goto J. et al., Drugs Exptl., Clin Res., XII (11), 917, 1986). Compared with this, the lipid emulsion of the present invention exhibits a significant efficacy in dosages of 1.0 μg/kg or more and has a stronger efficacy than LipoPGE$_1$. According to FIG. 4, the efficacy of the lipid emulsion of the present invention is about 2 to 3 times stronger than that of LipoPGE$_1$.

Example 4

The stability of the lipid emulsion of the isocarbacyclin methyl ester obtained in the same manner as in Example 1 was studied by the method shown below.

Storage conditions: 8±1°, transparent glass ampoules, in paper boxes (blocking light)

Storage samples: Each 1 ml and 2 ml of concentration of 2 μg/ml in each 3 lots

The content after 24 months was compared with that at the start. In the 1 ml ampoule group, it was 97.8 to 98.2%, while in the 2 ml ampoule group, it was 96.0 to 100.0%.

Example 5

Using the lipid emulsion of the isocarbacyclin methyl ester obtained in the same way as of Example 1, the effect on peripheral circulation disorders was evaluated by the generally used rat tail gangrene model. Further, a comparison was made in this model with LipoPGE1 which is a similar lipid preparation as the lipid emulsion of the present invention and is considered suitable for the same chronic arterial occlusion. Further, the LipoPGE1 1 used was prepared according to the method described in the examples of Japanese Unexamined Patent Publication (Kokai) No. 58-222014.

For the rat tail gangrene model, use was made of the following method based on a modification of a known method (Lund, F., Acta Physiologica Scandinavia, 23. Suppl. 82, 1 (1951)).

Rats (Wistar, male, body weight of 180 to 200 g) were anesthezied by halothane, then 100 μl of epinephrine (0.1 mg) was administered subcutaneously at both the ventral and dorsal sides of the portion 6 cm from the tip of the tail. At the same time, ergotamine (4.0 mg/kg) was administered subcutaneously at the back. The lipid emulsion of the present invention (or LipoPGE$_1$) was administered at five minutes before the administration of epinephrine and ergotamine and then from the following day once a day for 6 days by one shot from the femoral vein (amount of drug of 0.5 ml/kg). The efficacy of the lipid emulsion of the present invention was evaluated by measuring the length of gangrene of the rat tails every day and using this as the suppression of length of gangrene.

Figure 5:
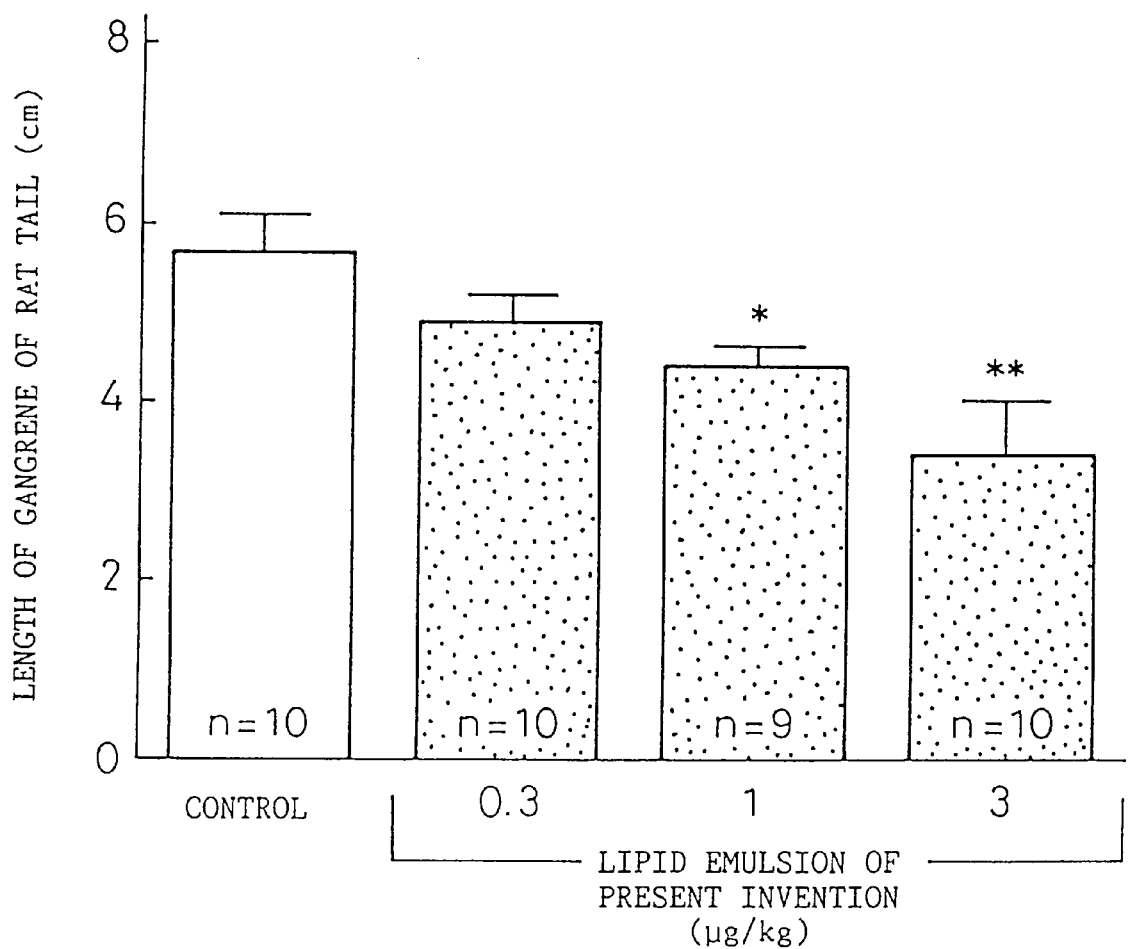
FIG. 5 is a view illustrating the effects of evaluation of the effect of the lipid emulsion of the present invention on peripheral circulation disorders by the rat tail gangrene model.
Figure 6:
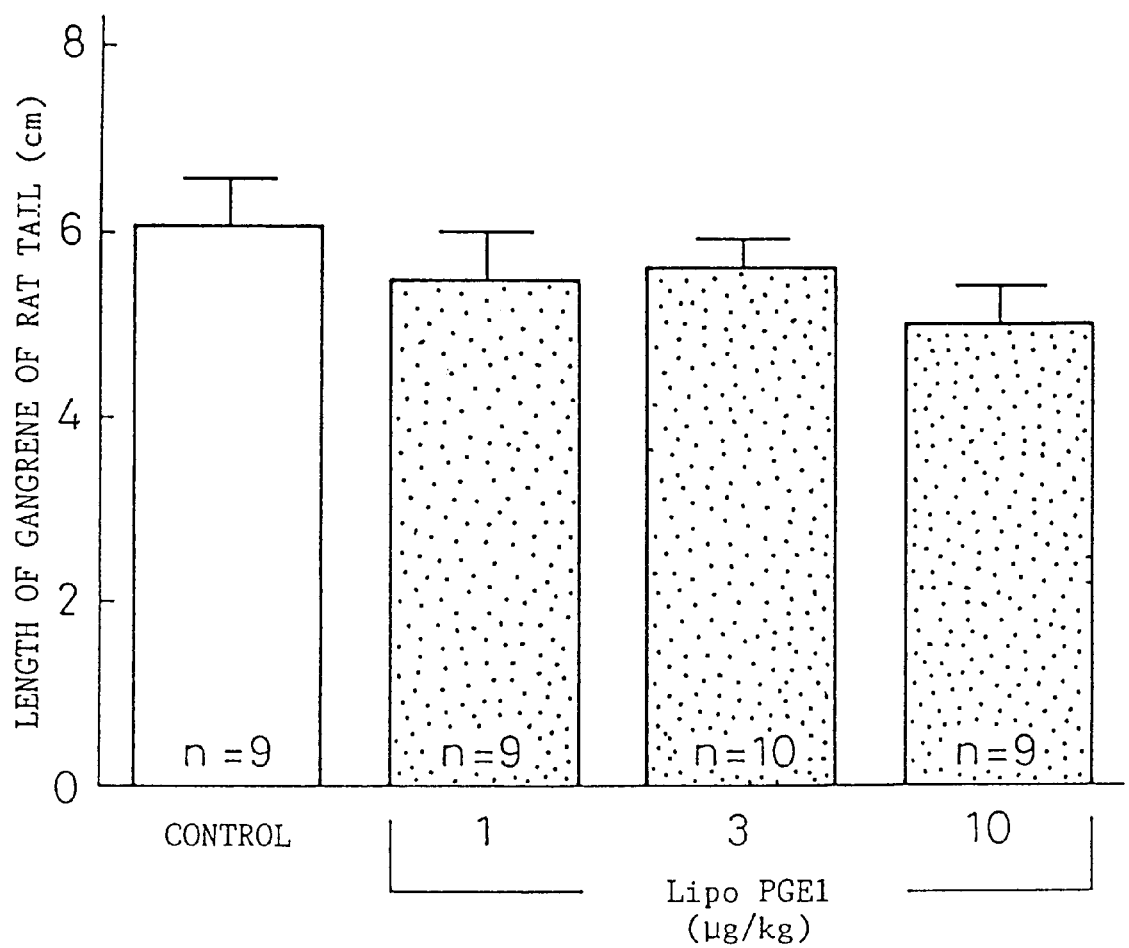
FIG. 6 is a view of the results of the evaluation of the effect of Lipo $PGE_1$ on peripheral circulation disorders by the rat tail gangrene model.

The results of evaluation in this model of the lipid emulsion of the present invention and LipoPGE$_1$ are shown in FIG. 5 and FIG. 6. Further, in these figures, for the control of the lipid emulsion of the present invention and LipoPGE1, use was made of lipid emulsions not containing the active ingredients. FIG. 5 and FIG. 6 show the length of tail gangrene at 7 days after the administration of epinephrine and ergotamine in the case of administration of various concentrations of the lipid emulsion of the present invention and LipoPGE1 by the average ± standard error of average. The statistical analysis was performed by using a one-way ANOVA Dunnett's test and comparing with a control group. In FIG. 5 and FIG. 6, for the results of the statistical analysis, P<0.05 is shown by * and P<0.01 by **.

From the results of FIG. 5 and FIG. 6, it is clear that the lipid emulsion of the present invention exhibits a significant efficacy in dosages of 1.0 μg/kg or more. Compared with this, LipoPGE$_1$ just showed a suppressive tendency even at a dosage of 10 μg/kg and no significant efficacy could be observed. From these results, it became clear that the lipid emulsion of the present invention has a stronger efficacy than LipoPGE$_1$ and that the efficacy of the lipid emulsion of the present invention in this model is above 10 times stronger than that of LipoPGE$_1$.

INDUSTRIAL APPLICABILITY

The pharmaceutical composition of the present invention containing the isocarbacyclin of formula (1) as an effective ingredient for treating chronic arterial occlusion has a slow release and lesion selectivity, so has a powerful action and enables effective treatment by small dosages.

We claim:

1. A method for treating chronic peripheral arterial occlusion comprising administering an emulsion containing an isocarbacyclin to a patient in need thereof, wherein the isocarbacyclin has the following formula (1):

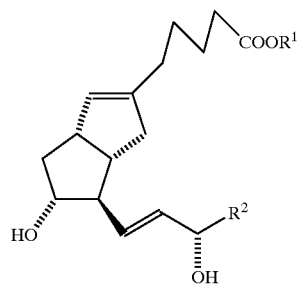

(1)

wherein $R^1$ is a hydrogen atom or a $C_1$ to $C_{10}$ alkyl group and $R^2$ is selected from the group consisting of substituted or unsubstituted $C_1$ to $C_{13}$ alkyl group, substituted or unsubstituted $C_2$ to $C_{13}$ alkenyl or alkynyl group, and substituted or unsubstituted $C_3$ to $C_{10}$ cycloalkyl group, in an amount of 0.2 to 1000 μg per ml of the composition, a vegetable oil in an amount of 0.05 to 0.5 g per ml of the composition, a phospholipid in an amount of 0.01 to 0.5 g per g of the vegetable oil, and water.

2. The method of claim 1, wherein $R^1$ is a hydrogen atom or a methyl group.

3. The method of claim 1, wherein $R^2$ is selected from the group consisting of n-pentyl, 2-methylhexyl, and cyclopentyl.

4. The method of claim 1, wherein $R^1$ is a methyl group and $R^2$ is an n-pentyl group.

5. The method of claim 1, wherein the isocarbacyclin is administered to a patient in need thereof in an amount of 0.1 to 5 μg per day.

6. A method for treating thromboangitis obliterans or arterioscle obliterans comprising administering an emulsion containing an isocarbacyclin to a patient in need thereof, wherein the isocarbacyclin has the following formula (1):

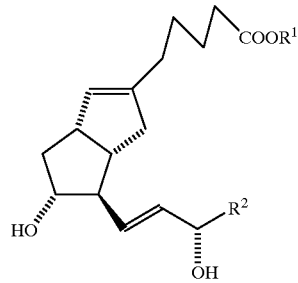

(1)

wherein $R^1$ is a hydrogen atom or a $C_1$ to $C_{10}$ alkyl group and $R^2$ is selected from the group consisting of substituted or unsubstituted $C_1$ to $C_{13}$ alkyl group, substituted or unsubstituted $C_2$ to $C_{13}$ alkenyl or alkynyl group, and substituted or unsubstituted $C_3$ to $C_{10}$ cycloalkyl group, in an amount of 0.2 to 1000 μg per ml of the composition, a vegetable oil in an amount of 0.05 to 0.5 g per ml of the composition, a phospholipid in an amount of 0.01 to 0.5 g per g of the vegetable oil, and water.

7. A method for treating ischemic ulcer accompanied with thromboangitis obliterans or arterioscle obliterans comprising administering an emulsion containing an isocabacyclin to a patient in need thereof, wherein the isocarbacyclin has the following formula (1):

(1) 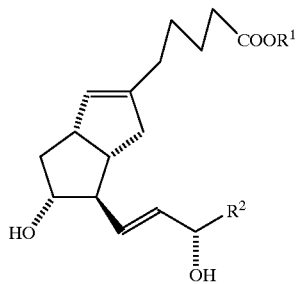

wherein $R^1$ is a hydrogen atom or a $C_1$ to $C_{10}$ alkyl group and $R^2$ is selected from the group consisting of substituted or unsubstituted $C_1$ to $C_{13}$ alkyl group, substituted or unsubstituted $C_2$ to $C_{13}$ alkenyl or alkynyl group, and substituted or unsubstituted $C_3$ to $C_{10}$ cycloalkyl group, in an amount of 0.2 to 1000 μg per ml of the composition, a vegetable oil in an amount of 0.05 to 0.5 g per ml of the composition, a phospholipid in an amount of 0.01 to 0.5 g per g of the vegetable oil, and water.

\* \* \* \* \*